US008471044B2

(12) United States Patent
Zaworotko et al.

(10) Patent No.: US 8,471,044 B2
(45) Date of Patent: Jun. 25, 2013

(54) EPIGALLOCATECHIN-3-GALLATE CRYSTAL COMPOSITIONS

(75) Inventors: Michael Zaworotko, Tampa, FL (US); Sheshanka Kesani, Tampa, FL (US)

(73) Assignee: University of South Florida, Tampa, FL (US)

( * ) Notice: Subject to any disclaimer, the term of this patent is extended or adjusted under 35 U.S.C. 154(b) by 541 days.

(21) Appl. No.: 12/602,951

(22) PCT Filed: Jun. 6, 2008

(86) PCT No.: PCT/US2008/007117
§ 371 (c)(1),
(2), (4) Date: Dec. 3, 2009

(87) PCT Pub. No.: WO2008/153938
PCT Pub. Date: Dec. 18, 2008

(65) Prior Publication Data
US 2010/0173984 A1 Jul. 8, 2010

Related U.S. Application Data

(60) Provisional application No. 60/942,355, filed on Jun. 6, 2007.

(51) Int. Cl.
*C07D 311/62* (2006.01)
(52) U.S. Cl.
USPC .......................................... 549/399; 514/456
(58) Field of Classification Search
USPC .......................................... 549/399; 514/456
See application file for complete search history.

(56) References Cited

U.S. PATENT DOCUMENTS

| 2003/0224006 A1 | 12/2003 | Zaworotko et al. |
| 2007/0026078 A1 | 2/2007 | Almarsson et al. |
| 2007/0059356 A1 | 3/2007 | Almarsson et al. |
| 2007/0299033 A1 | 12/2007 | McMahon et al. |
| 2008/0146772 A1 | 6/2008 | Zaworotko et al. |
| 2010/0204204 A1 | 8/2010 | Zaworotko et al. |
| 2010/0311701 A1 | 12/2010 | Almarsson et al. |

FOREIGN PATENT DOCUMENTS

| CN | 1367171 A | * | 9/2002 |
| CN | 1470510 | | 1/2004 |
| WO | 2007041891 A1 | | 4/2007 |

OTHER PUBLICATIONS

Bokuchava et al, Prikladnaya Biokhimiya I Mikrobiologiya, vol. 1 (2), p. 187-192 (1966) and English translation.*
Yao, et al., Epigallocatechin Gallate Protects Against Oxidative Stress-Induced Mitochondria-Dependent Apoptosis in Human Lens Epithelial Cells, Molecular Vision 2008: 217-23.
Potenza, et al., EGCG, a Green Tea Polyphenol, Improves Endothelial Function and Insulin Sensitivity, Reduces Blood Pressure, and Protects Against Myocardial I/R Injury in SHR, Am. J Physiol Endocrinol Metab 2007: 1378-1387.
Katiyar et al., Green Tea Polyphenol (–)Epigallocatechin-3-Gallate Treatment of Human Skin Inhibits Ultraviolet Radiation-Induced Oxidative Stress, Carcinogenesis 2001; vol. 22: 287-294.
Rezai-Zedeh et al., Green Tea Epigallocatechin-3-Gallate (EGCG) Modulates Amyloid Precursor Protein Cleavage and Reduces Cerebral Amyloidosis in Alzheimer Transgenic Mice, Journal of Neuroscience, 2005; 8807-8814.
Collins et al., Epigallocatechin-3-Gallate (EGCG), a Green Tea Polyphenol, Suppresses Hepatic Gluconeogenesis through 5'-AMP-activated Protein Kinase, Journ. Biological Chemistry, 2007; vol. 282, 30143-30149.
International Search Report issued Dec. 12, 2010 on PCT/US2008/007117.
Almarsson et al., Crystal engineering of the composition of pharmaceutical phases. Do pharmaceutical co-crystals represent a new path to improved medicines?, Chemical Communications, 2004, 1889-1896.
Anastas et al., Green Chemistry Theory and Practice, Chapter 4 Principles of green chemistry, 2000, 29-55, Oxford University Press, USA.
Borah et al., Microwave-induced one-pot synthesis of N-carboxyalkyl maleimides and phthalimides, Journal of Chemical Research, 1998, 272-273.
Chandrasekhar et al., Sovent free N-alkyl and N-arylimides preparation for anhydrides catalyzed by TaCl5-Silica gel, Tetrahedron Letters, 1997, 38(46), 8089-8092.
Childs et al., Crystal engineering approach to forming cocrystals of amine hydrocholorides with organic acids. Molecular compleses of fluoxetine hydrochloride with benzoic, succinic, and fumaric acids, Journal of American Chemical Society, 2004, 8 pages.
Dressman et al., Dissolution testing as a prognostic tool for oral drug absorption: Immediate release dosage forms, Pharmaceutical Research, 1998, 15(1), 11-22.
Etter et al., Solid-state nucleophilic aromatic substitution reaction of a carboxylic acid cocrystal, Tetrahedron Letters, 1989, 30(28), 3617-3620.
Fowler et al., A rational design of molecular materials, Journal of Physical Organic Chemistry, 2000, 13, 850-857.
Kaupp, Organic solid-state reactions with 100% yield, Top. Curr. Chem, 2005, 254, 95-183.
Kaupp et al., Waste-free and facile solid-state protection of diamines, anthranilic acid, diols, and polyols and phenylboronic acid, Chem. Eur. J., 2003, 4156-4160.
Kaupp et al., Quantitative solid-state reactions of amines with carbonyl compounds and isothiocyanates, Tetrahedron 56, 2000, 6899-6911.
Li et al., Solid-state acid-base interactions in complexes of heterycyclic bases with bicarboxylic acids: Crystallography, hydrogen bond analysis, and 15N NMR Spectroscopy, Journal of American Chemistry Society, 2006, 128, 8199-8210.
MacGillivray et al., Supramolecular control of reactivity in the solid state using linear molecular templates, Journal of American Chemistry Society, 2000, 122, 7817-7818.
Remenar et al., Crystal engineering of novel cocrystals of triazole drug with 1,4-dicarboxylic acids, Journal of American Chemistry Society, 2003, 125, 8456-8457.

(Continued)

*Primary Examiner* — Bernard Dentz
(74) *Attorney, Agent, or Firm* — Bryan Cave LLP

(57) ABSTRACT

Crystalline epigallocatechin-3-gallate compositions and methods of use.

17 Claims, 24 Drawing Sheets

OTHER PUBLICATIONS

Shan et al., Mechanochemistry and co-crystal formation: effect of solvent on reaction kinetics, ChemComm, 2002, 2372-2373.

Tanaka et al., Solvent-free organic synthesis, Chemical Review, 2000, 100, 1025-1074.

Vidal et al., Re-examination of microwave-induced synthesis of phthalimides, Tetrahedron 56, 2000, 5473-5478.

Vishweshwar et al., Pharmaceutical co-crystals, Journal of Pharmaceutical Sciences, 2006, 95(3), 499-516.

Yao et al., Epigallocatechin gallate protects against oxidative stress-induced mitochondria-dependent apoptosis in human lens epithelial cells, Molecular Vision, 2008, 14, 217-223.

* cited by examiner

US 8,471,044 B2

EPIGALLOCATECHIN-3-GALLATE CRYSTAL COMPOSITIONS

CROSS-REFERENCE TO RELATED APPLICATIONS

This application claims the benefit of U.S. Provisional Patent Application Ser. No. 60/942,355 filed Jun. 6, 2007, which is incorporated herein by reference in its entirety.

FIELD OF THE INVENTION

The present invention is generally related to epigallocatechin-3-gallate (EGCG), a catechin with antioxidant effects found in green tea, and more particularly to novel solvated and non-solvated crystalline forms of EGCG. Such compositions may be used in the preparation of (or even as) pharmaceuticals, nutraceuticals, nutritional supplements, food compositions and the like.

BACKGROUND OF THE INVENTION

It is well established that some organic compounds can crystallize in a number of different polymorphic forms or crystal habits, which may comprise the compound as such, solvates of the compound, hydrates of the compound, or combinations thereof. Alternatively, the compound, solvate or hydrate may exist as an amorphous solid.

When a compound containing crystal polymorphs is used as a nutraceutical, it is often necessary to produce a substance having a specific crystal form to guarantee the consistency of physicochemical and biological properties of the compound. Furthermore, in the process of manufacturing a drug substance, it is often important to separate out a particular form of crystal during the crystallization procedure, in order to maintain defined levels of the yield and purification efficiency.

Green tea, the beverage made from the unfermented leaves of *Camellia sinensis*, contains many constituents, including polyphenols which are commonly known as catechins or flavonoids. Catechins are thought to be responsible for many of the biological effects of tea. Epigallocatechin-3-gallate (EGCG) is the major catechin from green tea. EGCG is a compound of interest among the green-tea-derived catechins because it exhibits a strong antioxidant effect. Furthermore, EGCG has been associated with beneficial antioxidant, anti-inflammatory, and anti-carcinogenic effects. Yao et al. demonstrated that EGCG protects against oxidative stress-induced mitochondria-dependent apoptosis (2008); Potenza et al. found that EGCG improves endothelial function and insulin sensitivity, reduces blood pressure, and protects against myocardial ischemia-reperfusion injury in a mouse model of metabolic syndrome (2007); Katiyar et al. found that EGCG inhibits the effects of oxidative stress and prevents carcinogenesis (2001); Rezai-Zadeh et al. further studied EGCG's use in preventing and treating neurodegenerative diseases by showing that EGCG modulates amyloid precursor protein cleavage and reduces cerebral amyloidosis in a mouse model of Alzheimer's disease (2005); and Collins et al. demonstrated that EGCG suppresses hepatic gluconeogenesis by activating the 5'-AMP-activated protein kinase (AMPK) (2007). Elucidation of these molecular actions of EGCG substantiates the compound as a versatile modulator of cellular responses that may contribute to disease pathogenesis. Alzheimer's disease (AD) is a devastating neurodegenerative disease that currently affects an estimated 4.5 million Americans, costing the U.S. more than $100 billion annually. Finding a treatment that could delay onset by five years could reduce the number of individuals with AD by nearly 50 percent after 50 years. A promising approach to drug development for AD is to screen natural compounds, such as EGCG, which already have some available information regarding toxicity, metabolism, and possible therapeutic efficacy. In addition, EGCG and caffeine are effective in reducing beta-amyloid levels and plaque formation in transgenic mouse models of Alzheimer's disease.

Depending on the administration route desired in therapy utilizing EGCG, it may be desirable to improve or at least control the stability and water solubility of the EGCG to obtain a desired bioavailability profile. Furthermore, it can assist the manufacturing or purification process if the stability and water solubility of the EGCG can be controlled. In principle, the water solubility of polymorphic forms of an organic compound is not necessarily the same for all forms. Therefore, the use of specific crystalline forms or habits can offer useful control of the water solubility. Even a slight adjustment to the water-solubility by means of an adjustment to the polymorphic form can offer useful processing or biological advantages.

SUMMARY OF THE INVENTION

Among the various aspects of the invention is the provision of crystalline EGCG, including the provision of solvated and non-solvated crystalline forms of EGCG, and the provision of a process for the preparation of such solvated and non-solvated crystalline forms. These crystalline forms possess a range of desirable properties and may be used as a nutraceutical, as part of a pharmaceutical composition, nutritional supplements, foodstuffs, and the like.

In a first aspect, the present invention is directed to crystalline EGCG.

The present invention is further directed to a process for the preparation of a crystal form of EGCG, wherein the process comprises dissolving EGCG in a solvent and precipitating crystalline EGCG from the solution.

The present invention is further directed to a pharmaceutical composition comprising crystalline EGCG. Typically, the pharmaceutical composition comprises one or more pharmaceutically acceptable carriers.

The present invention is further directed to a method for treating a disease or condition resulting from oxidative stress. In this method, a pharmaceutical, foodstuff or nutraceutical composition comprising crystalline EGCG is administered to a person or animal having or predisposed to having a condition resulting from oxidative stress.

The present invention is further directed to a method for improving animal health or nutrition.

Other aspects and objects of the invention will be in part apparent and in part pointed out hereinafter.

DETAILED DESCRIPTION OF THE PREFERRED EMBODIMENTS

Figure 1:
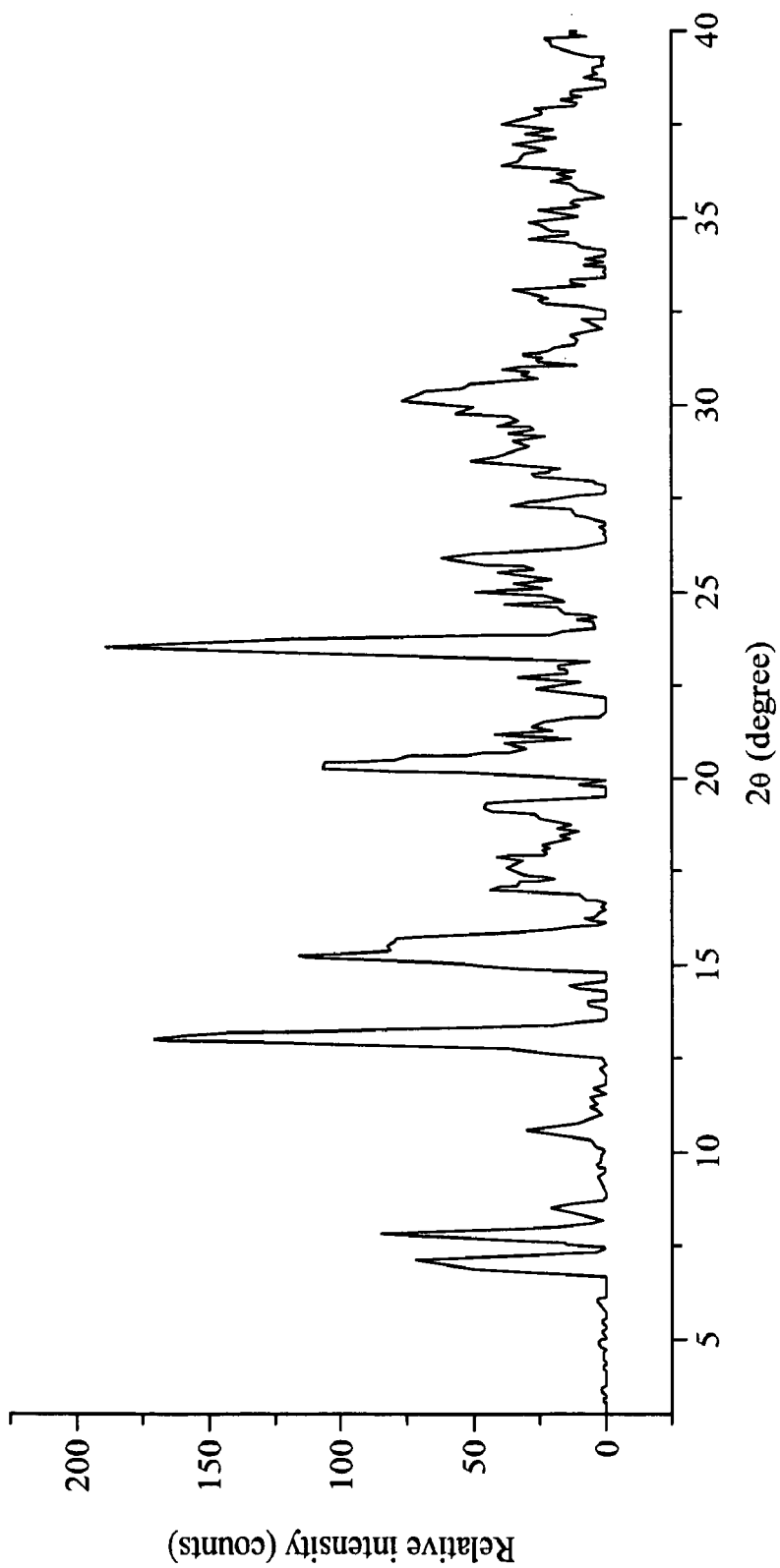
FIG. 1 shows an experimental XRPD pattern of a sample of EGCG in crystal form II, exhibiting major peaks at about the following positions: 7.1, 7.8, 10.5, 13.0, 15.2, 20.3, 23.5 and 25.9.

In accordance with one aspect of the present invention, novel crystalline forms of EGCG are provided. The crystalline forms may be solvated or non-solvated. Advantageously, these crystalline forms may be prepared in pharmaceutical or edible grade and thus may be used in the preparation of pharmaceuticals, nutraceuticals, nutritional supplements, foodstuffs and the like. Additionally, the crystalline forms may be hydrated to various degrees and in various physical forms. Thus, for example, EGCG may be obtained as an isolated, dry solid or as a crystal slurry.

In general, it is preferred that EGCG be in the form of a solvated or non-solvated crystalline material and that the crystalline material contain at least about 50% by weight EGCG. For example, in one embodiment, it is preferred that the crystalline material contain at least about 50% by weight EGCG. In certain embodiments, greater degree of purity may be desired; in such instances, it may be preferred that the crystalline material contain at least about 80% by weight EGCG, at least about 90% by weight EGCG, at least about 95% by weight EGCG, or even at least about 98% by weight EGCG. By way of further example, it may be preferred that the crystalline material contain at least about 99% by weight EGCG.

In general, it is preferred that the EGCG crystal contain less than a stoichiometric amount of water. For example, in one embodiment, it is preferred that the crystalline material contain less than 1% by weight water. In certain embodiments, lesser degrees of hydration may be desired; in such instances, it may be preferred that the crystalline material contain less than 0.5% by weight water, less than 0.1% by weight water, less than 0.05% by weight water, or even less than 0.01% by weight water.

The forms of EGCG provided by the present invention possess a number of advantageous properties, particularly with respect to stability and handling characteristics. Consequently, these advantages may be exploited in connection with the manufacturing, purification, formulation and storage phases of the marketed EGCG compositions and/or to the delivery of the EGCG from the composition to the human or non-human animal patient for achieving the desired biological, pharmacological or nutritional effect.

The present invention provides for using forms of EGCG to treat or prevent Alzheimer's Disease, or in any disease that would benefit from a reduction in beta-amyloid levels and/or plaque formation in the brain, in a human or animal.

The present invention also provides methods for preparing the materials of the present invention, preferably by precipitation of EGCG from a solution of EGCG in an appropriate organic solvent or solvent mixture or by other crystallization of EGCG in an appropriate organic solvent or solvent mixture, optionally in the presence of water, as well as medicaments, nutraceuticals, nutritional supplements, foodstuffs and beverages containing the said materials, methods of preparing the medicaments, nutraceuticals, nutritional supplements, foodstuffs and beverages, uses of the said materials in the preparation of the medicaments, nutraceuticals, nutritional supplements, foodstuffs and beverages, and uses of the medicaments, nutraceuticals, nutritional supplements, foodstuffs and beverages in human and veterinary medicine and in non-therapeutic human and non-human animal treatments.

The materials according to the present invention may therefore conveniently be present in substantially pure isolated form. The materials may suitably be prepared on a kilogram scale.

Solvated Crystal Forms

In a preferred embodiment, EGCG is in the form of a solvated crystal. In general, the solvated crystal is characterized by the presence of a solvent or solvents entrapped in the crystal structure. The solvent contained by the solvated crystalline form may be any organic solvent. In one preferred embodiment, the solvent is chosen from the group including, but not limited to, nitriles (e.g. acetonitrile, benzonitrile, etc.), ketones (e.g. acetone, methylethyl ketone, etc.), amides (e.g. N,N-dimethylformamide, N,N-dimethylacetamide, etc.), alcohols (e.g. methanol, ethanol, 1-propanol, 2-propanol, etc.), organochlorides (chloroform, dichloromethane, dichloroethene, trichloroethane, etc.), ethers (e.g., tetrahydrofuran), nitrobenzene, or a mixture thereof. In another embodiment, the solvent is selected from the group consisting of nitriles, organochlorides, nitrobenzene and combinations thereof. In a further embodiment, the solvent is acetonitrile, nitrobenzene, dichloromethane, or a combination thereof.

Solvated crystal forms are characterized by having a stoichiometric ratio of solvent to EGCG on a molar equivalent basis. In a preferred embodiment, the molar ratio of solvent to EGCG is generally within the range of about 0.5:1 to about 5:1, respectively. In certain embodiments, the molar ratio of solvent to EGCG will be less than 4:1, respectively. In other embodiments, the molar ratio will be less, e.g., less than 3:1, 2:1 or even less than 1:1, respectively. In certain embodiments, the molar ratio of solvent to EGCG will be still less, e.g., less than 1:1.5, 1:2, 1:3, 1:4, or even 1:5, respectively.

The crystal lattice may include lattice vacancies. In general, no more than 20% of the lattice positions will be vacancies. More typically, the crystal will have less than 10% vacancies. In one embodiment, for example, the crystal lattice has less than 5% vacancies, less than 1% vacancies or even less than 0.1% vacancies.

In some embodiments, non-aqueous, non-solvent impurities are present in the EGCG solvated crystal. In one embodiment, epicatechin gallate (ECG) molecules are substituted for a percentage of the EGCG molecules in the crystalline structure. ECG is a catechin also found in green tea, but is usually present in lower concentrations than EGCG. In preferred embodiments, the solvated crystal packing structure is substantially unchanged by this substitution. In general, it is preferred that the solvated crystal form contains less than 20 mole % ECG impurities. In certain embodiments, greater degree of purity may be desired; in such instances, it may be preferred that the crystalline material contain less than 10 mole % ECG impurities, less than 5 mole % ECG impurities; or even less than 1 mole % ECG impurities.

In another embodiment, non-aqueous, non-solvent, non-ECG impurities may be present in the EGCG solvated crystal. In general, it is preferred that the solvated crystal form contains less than 1 wt % non-aqueous, non-solvent, non-ECG impurities. In certain embodiments, greater degree of purity may be desired; in such instances, it may be preferred that the crystalline material contain less than 0.5 wt % non-aqueous, non-solvent, non-ECG impurities; less than 0.1 wt % non-aqueous, non-solvent, non-ECG impurities; or even less than 0.01 wt % non-aqueous, non-solvent, non-ECG impurities.

In one particularly preferred embodiment, the solvated crystal corresponds to a solvated crystalline form designated as Form II herein. Form II has an X-ray powder diffraction (XRPD) pattern substantially as shown in FIG. 1 of the accompanying drawings, exhibiting major peaks at about the following positions: 7.1, 7.8, 10.5, 13.0, 15.2, 20.3, 23.5, and 25.9. Further characterization of Form II, by Fourier Transform infrared spectroscopic analysis (FT-IR), thermogravimetric analysis (TGA), differential scanning calorimetry (DSC), and single crystal x-ray diffraction analysis, are found in Example 1.

Figure 6:
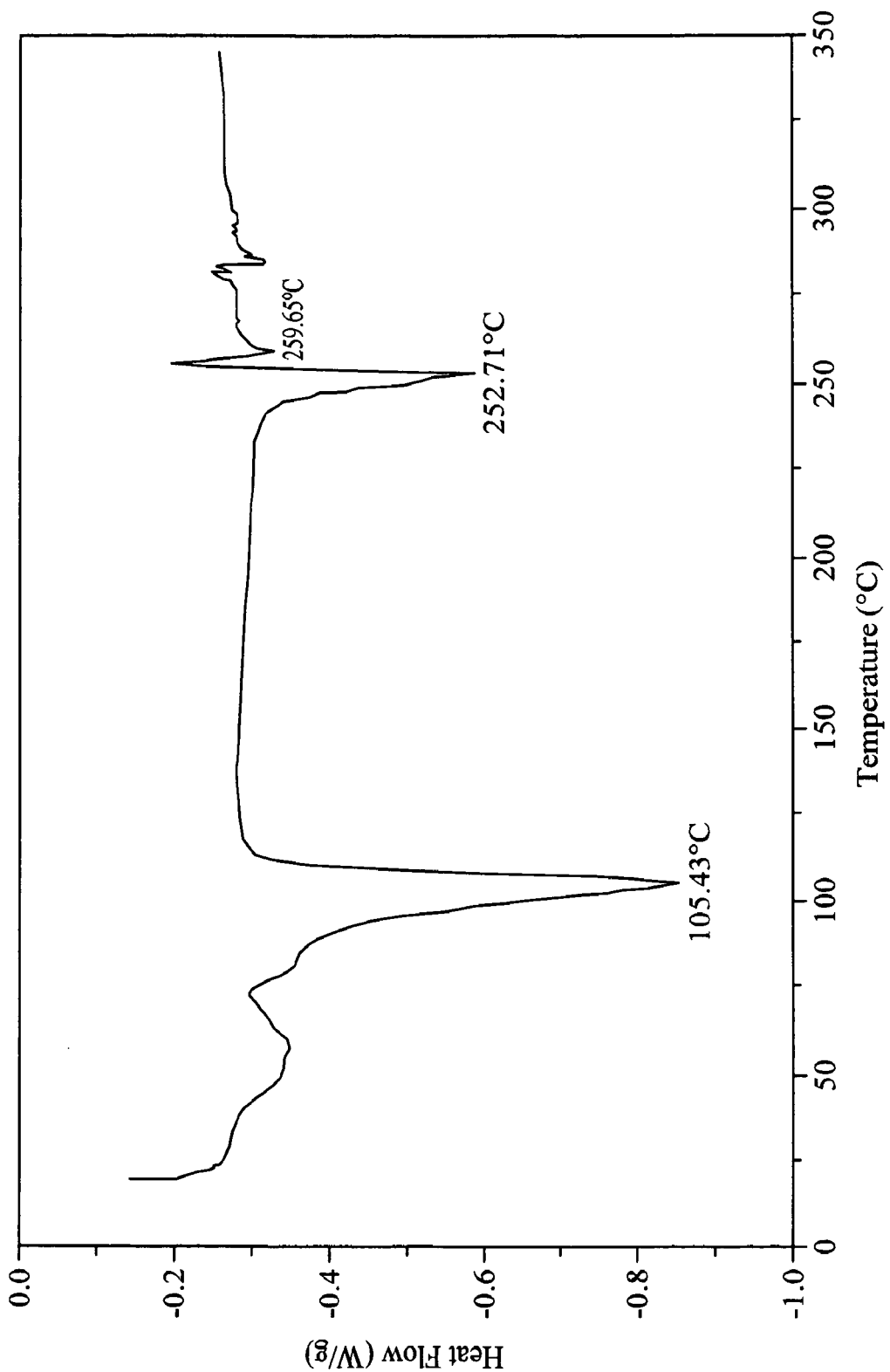
FIG. 6 shows a DSC thermogram of a sample of EGCG in crystal form II, with phase changes observed at about 105° C. and about 253° C. as described more fully in Example 1.

In another particularly preferred embodiment, the solvated crystal corresponds to a solvated crystalline form designated as Form III herein. Form III has an XRPD pattern substantially as shown in FIG. 6 of the accompanying drawings, exhibiting major peaks at about the following positions: 13.4, 15.4, 19.4, 24.3, 27.8, 28.5, 31.3, and 37.5. Further characterization of Form III, by FT-IR, TGA, DSC, and single crystal x-ray diffraction analysis, are found in Example 2.

Unsolvated Crystal Forms

In another preferred embodiment, EGCG is in a crystalline form that substantially lacks solvate. For example, in one embodiment, it is preferred that the crystalline material contain less than 1% solvent by weight. In certain embodiments, greater degree of purity may be desired; in such instances, it may be preferred that the crystalline material contain less than 0.5% solvent by weight, less than 0:1% solvent by weight, less than 0.05% solvent by weight, or even less than 0.01% solvent by weight.

Figure 11:
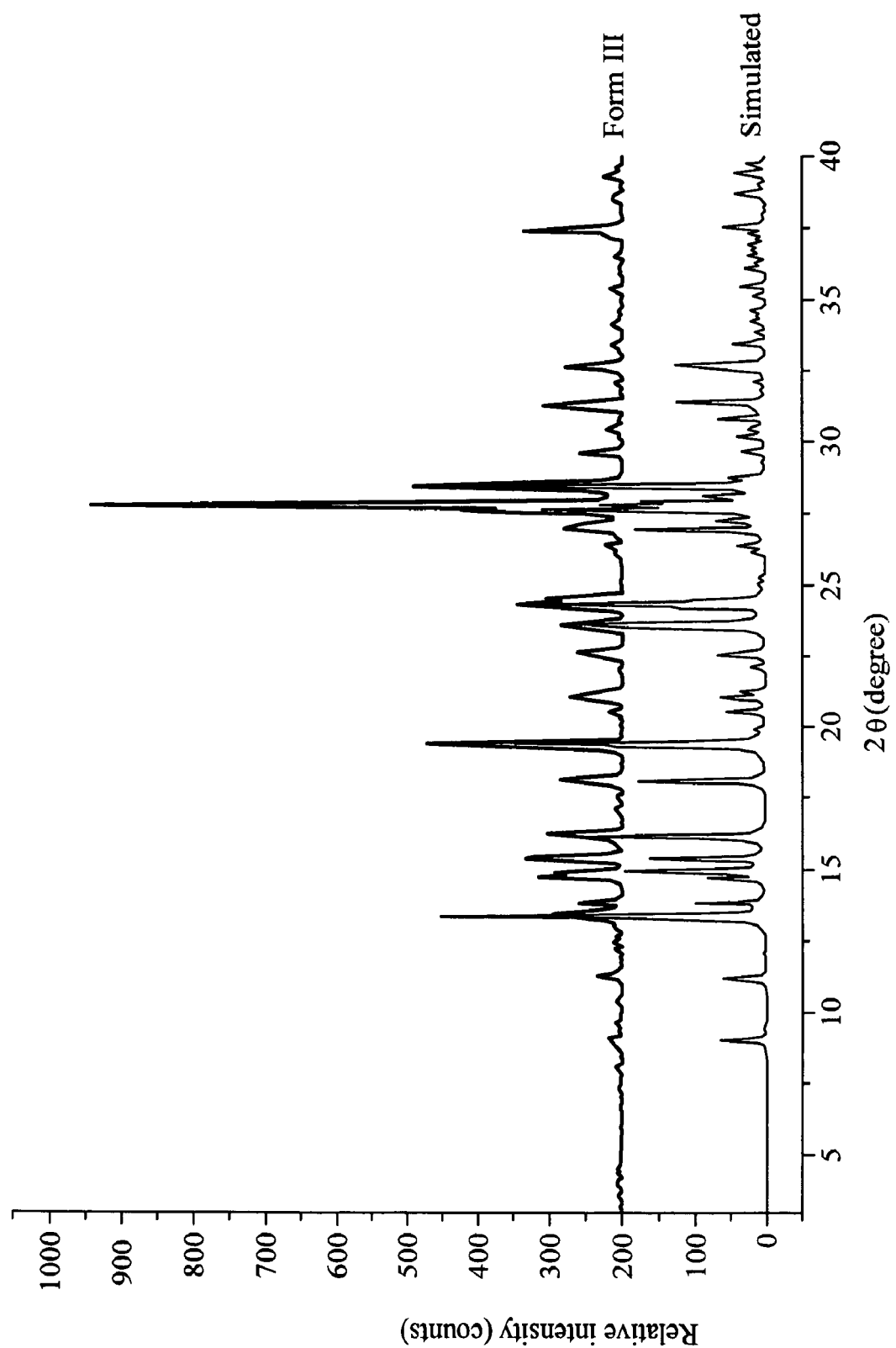
FIG. 11 shows a comparison of the experimental and calculated XRPD patterns for crystal form III as described more fully in Example 2.

In a particularly preferred embodiment, the unsolvated crystalline form corresponds to a crystal form designated as Form IV herein. Crystal Form IV has an XRPD pattern substantially as shown in FIG. 11 of the accompanying drawings, exhibiting major peaks at about the following positions: 13.9, 17.2, 21.2, 23.6, 26.5, 29.0, and 31.5. Further characterization of Form IV, by FT-IR, TGA, DSC, and single crystal x-ray diffraction analysis, are found in Example 3.

In some embodiments, non-aqueous, non-solvent impurities are present in the EGCG unsolvated crystal. In one embodiment, ECG molecules are substituted for a percentage of the EGCG molecules in the crystalline structure. In preferred embodiments, the solvated crystal packing structure is substantially unchanged by this substitution. In general, it is preferred that the EGCG crystal contains less than 20 mole % ECG. In certain embodiments, greater degree of purity may be desired; in such instances, it may be preferred that the crystalline material contain less than 10 mole % ECG, less than 5 mole % ECG, less than 2 mole % ECG; or even less than 1 mole % ECG.

In another embodiment, non-aqueous, non-solvent, non-ECG impurities may be present in the EGCG unsolvated crystal. In general, it is preferred that the solvated crystal form contains less than 1% by weight non-aqueous, non-solvent, non-ECG impurities. In certain embodiments, greater degree of purity may be desired; in such instances, it may be preferred that the crystalline material contain less than 0.5% by weight non-aqueous, non-solvent, non-ECG impurities; less than 0.1% by weight non-aqueous, non-solvent, non-ECG impurities; or even less than 0.01% by weight non-aqueous, non-solvent, non-ECG impurities.

Methods of Preparing Solvated Crystal Forms

A substantially and crystallographically pure crystal form II of EGCG Form I can be manufactured in a stable manner by dissolving Form I in an organic solvent, then precipitating the crystals. As used herein, "EGCG Form I" refers to a reference form of EGCG. This organic solvent is preferably chosen from the group including, but not limited to, organochlorides (chloroform, dichloromethane, dichloroethene, trichloroethane, etc.), nitriles (e.g. acetonitrile, benzonitrile, etc.), ketones (e.g. acetone, methylethyl ketone, etc.), amides (e.g. N,N-dimethylformamide, N,N-dimethylacetamide, etc.), alcohols (e.g. methanol, ethanol, 1-propanol, 2-propanol, etc.), or a mixture thereof. The use of a nitrile for the organic solvent is more preferred, with acetonitrile even more preferred.

Methods of precipitating crystals are well known to those of skill in the art. For example, crystals may be precipitated by evaporation, by heating or cooling, by diffusion, or by a mixture or processes thereof. In one embodiment, a second organic solvent is added to the solution of Form I and the first organic solvent before cooling for a retention time. In an alternate embodiment, the first organic solvent is evaporated.

The second organic solvent is preferably chosen from the group including, but not limited to, organochlorides (chloroform, dichloromethane, dichloroethene, trichloroethane, etc.), nitriles (e.g. acetonitrile, benzonitrile, etc.), ketones (e.g. acetone, methylethyl ketone, etc.), amides (e.g. N,N-dimethylformamide, N,N-dimethylacetamide, etc.), alcohols (e.g. methanol, ethanol, 1-propanol, 2-propanol, etc.), nitroaromatics (e.g. nitrobenzene) or a mixture thereof. The use of an organochloride for the second organic solvent is more preferred, with dichloromethane even more preferred.

There is no particular limitation on the retention time so long as it can ensure the transition from EGCG Form I to the crystalline form; however it is preferably at least one hour, more preferably at least 72 hours. There is no defined upper limit on the retention time; however, from the economic point of view, it is preferably seven days or less, more preferably three days or less.

In order to increase the yield, crystals can be grown using seed crystals of solvated EGCG already crystallized by further adding a poor solvent, such as water, or by cooling the solution after crystals have come out.

After crystallization, the filtrate is removed by a conventional method, for example, centrifugation or filtration, and the crystals are dried by a conventional drying method, such as vacuum drying or hot air drying, to obtain the desirable crystal form.

Methods of Preparing Unsolvated Crystal Forms

In one embodiment, a substantially and crystallographically pure unsolvated crystal form of EGCG can be manufactured in a stable manner by dissolving a solvated EGCG crystal form in an organic solvent, then precipitating the crystals. This organic solvent is preferably chosen from the group including, but not limited to, organochlorides (chloroform, dichloromethane, dichloroethene, trichloroethane, etc.), nitriles (e.g. acetonitrile, benzonitrile, etc.), ketones (e.g. acetone, methylethyl ketone, etc.), amides (e.g. N,N-dimethylformamide, N,N-dimethylacetamide, etc.), alcohols (e.g. methanol, ethanol, 1-propanol, 2-propanol, etc.), nitroaromatics (e.g. nitrobenzene) or a mixture thereof. The use of a nitrile for the organic solvent is more preferred, with acetonitrile even more preferred.

To prepare the crystals, any method known to one of skill in the art may be used. In one embodiment, the solution of a solvated EGCG crystal form and an organic solvent is heated to dryness to produce unsolvated crystals. In another embodiment, the crystals of a solvated EGCG crystal form are placed under a vacuum. In a further embodiment, the unsolvated crystals of EGCG are prepared using both heat and a vacuum. In a preferred embodiment, solvated EGCG crystals are heated to the range of 50° C. to 60° C. in a vacuum oven and the crystals of unsolvated EGCG are thereby prepared.

In an alternate embodiment, unsolvated EGCG crystal form can be manufactured by adding seed crystals of unsolvated EGCG crystals (Form IV) to a saturated solution of EGCG Form I and an organic solvent or by adding seed crystals to a saturated solution of EGCG From II and an organic solvent or by adding seed crystals to a saturated solution of EGCG Form II and an organic solvent.

This organic solvent is preferably chosen from the group including, but not limited to, organochlorides (chloroform, dichloromethane, dichloroethene, trichloroethane, etc.), nitriles (e.g. acetonitrile, benzonitrile, etc.), ketones (e.g. acetone, methylethyl ketone, etc.), amides (e.g. N,N-dimethylformamide, N,N-dimethylacetamide, etc.), alcohols (e.g. methanol, ethanol, 1-propanol, 2-propanol, etc.), nitroaromatics (e.g. nitrobenzene) or a mixture thereof. The use of an organochloride for the second organic solvent is more preferred, with dichloromethane even more preferred.

There is no particular limitation on the retention time so long as it can ensure the transition from solvated EGCG crystal form to the unsolvated crystal form; however it is preferably at least one hour, more preferably at least three days. There is no defined upper limit on the retention time; however, from the economic point of view, it is preferably fourteen days or less, more preferably ten days or less.

After crystallization, the filtrate is removed by a conventional method, for example, centrifugation or filtration, and the crystals are dried by a conventional drying method, such as vacuum drying or hot air drying, to obtain the desirable unsolvated crystal form.

Pharmaceutical, Foodstuffs, and Nutraceutical Compositions

In addition, the present invention provides a pharmaceutical, foodstuff, nutritional supplement, and nutraceutical compositions comprising crystalline EGCG, as described above, as an active ingredient. In a preferred embodiment, the crystalline form is crystal form IV of EGCG, as described above, as an active ingredient.

EGCG can be used for prevention or therapy of various diseases, based on its antioxidant effects. It is useful for treatment or prevention of diseases including, but not limited to: a neurodegenerative disease or condition such as Alzheimer's disease; an upper respiratory disease, such as one caused by an infection; a dementia, such as AIDS-dementia; an oncological disorder, such as cancer; inflammatory or auto-immune diseases, such as rheumatoid arthritis or diabetic neuropathies; or a disease or condition caused by an infection by virus or bacteria. EGCG may also be used, alone or in combination with other compositions, to improve animal health or nutrition.

The active agent prepared according to the present invention may thus be formulated into any suitable composition form for administration to a human or non-human animal patient.

The composition may consist of the active agent alone or may include the active agent and any suitable additional component, such as one or more pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Each carrier must be acceptable in the sense of being compatible with the other ingredients of the formulation and not injurious to the patient.

Excipients employed in the compositions of the present invention can be solids, semi-solids, liquids or combinations thereof. Preferably, the excipients are solids. Compositions of the invention containing excipients can be prepared by any known technique that comprises, for example, admixing an excipient with EGCG. A pharmaceutical, foodstuff, nutritional supplement, or nutraceutical composition of the invention contains a desired amount of EGCG and, optionally, an active pharmaceutical ingredient ("API") or other nutraceutical composition per dose unit and, if intended for oral administration, can be in the form, for example, of a tablet, a caplet, a pill, a hard or soft capsule, a lozenge, a cachet, a dispensable powder, granules, a suspension, an elixir, a dispersion, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of EGCG, such as tablets or capsules.

Compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colorcon™ 1500), clays (e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a co-crystal of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Avalon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition.

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Compositions of the invention optionally comprise one or more pharmaceutically acceptable wetting agents as excipients. Such wetting agents are preferably selected to maintain the crystal in close association with water, a condition that is believed to improve bioavailability of the composition. Such wetting agents can also be useful in solubilizing or increasing the solubility of crystals.

Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and degrees Ctoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

Compositions of the invention optionally comprise one or more pharmaceutically acceptable lubricants (including antiadherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

The composition may, for example, be a pharmaceutical composition (medicament), a foodstuff, food supplement or beverage. The terms "foodstuff", "food supplement", "nutritional supplement", and "beverage" used herein have the normal meanings for those terms, and are not restricted to pharmaceutical preparations. The appropriate pharmaceutical or edible grade of ingredients will be used, according to the desired composition form.

Pharmaceutical compositions according to the present invention include formulations suitable for oral, rectal, intranasal, topical (including transdermal, buccal and sublingual), vaginal, parental (including subcutaneous, intramuscular, intravenous and intradermal) and pulmonary administration. The formulations can conveniently be presented in unit dosage form and can be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with a suitable carrier, such as liquid carriers or finely divided solid carriers or both, and then if necessary shaping the product. Formulations of the subject invention suitable for oral administration can be presented as discrete units such as capsules, cachets or tablets, each containing a predetermined amount of the active ingredient; or as an oil-in-water liquid emulsion, water-in-oil liquid emulsion, or as a supplement within an aqueous solution, for example, a tea. The active ingredient can also be presented as bolus, electuary, or paste.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; mouthwashes comprising the active ingredient in a suitable liquid carrier; and chocolate comprising the active ingredients.

Formulations suitable for topical administration according to the subject invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents. Topical formulations preferably comprise compounds that facilitate absorption of the active ingredients through the skin and into the bloodstream.

Formulations suitable for intranasal administration, wherein the carrier is a solid, include a coarse powder having a particle size, for example, in the range of about 20 to about 500 microns, which is administered in the manner in which snuff is taken, i.e., by rapid inhalation through the nasal passage from a container of the powder held close up to the nose. Suitable formulations wherein the carrier is a liquid for administration by nebulizer, include aqueous or oily solutions of the agent. Formulations preferably comprise compounds that facilitate absorption of the active ingredients through the skin and into the bloodstream.

Formulations suitable for parenteral administration include aqueous and non-aqueous isotonic sterile injection solutions which can contain antioxidants, buffers, bacteriostats and solutes which render the formulation isotonic with the blood of the intended recipient; and aqueous and non-aqueous sterile suspensions which can include suspending agents and thickening agents, and liposomes or other microparticulate systems which are designed to target the compound to blood components or one or more organs. The formulations can be presented in unit-dose or multi-dose or multi-dose sealed containers, such as for example, ampoules and vials, and can be stored in a freeze-dried (lyophilized) condition requiring only the addition of the sterile liquid carrier, for example, water for injections, immediately prior to use. Extemporaneous injection solutions and suspensions can be prepared from sterile powders, granules and tablets of the kind previously described.

It should be understood that in addition to the ingredients particularly mentioned above, the formulations useful in the present invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Various delivery systems are known in the art and can be used to administer a therapeutic agent or composition of the invention, e.g., encapsulation in liposomes, microparticles, microcapsules, receptor-mediated endocytosis and the like. Methods of administration include, but are not limited to, parenteral, intra-arterial, intramuscular, intravenous, intranasal, and oral routes. The pharmaceutical compositions can be provided in the form of tablets, lozenges, granules, capsules, pills, ampoule, suppositories or aerosol form. The pharmaceutical compositions can also be provided in the form of suspensions, solutions, and emulsions of the active ingredient in aqueous or non-aqueous diluents, syrups, granulates or powders.

In one embodiment, the EGCG-containing compositions of the invention can be administered locally to the area in need of treatment; such local administration can be achieved, for example, by local infusion during surgery, by injection, or by means of a catheter. In another embodiment, a compound or composition of the invention is administered in a manner so as to achieve peak concentrations of the active compound at sites of the disease. Peak concentrations at disease sites can be achieved, for example, by intravenously injecting of the agent, optionally in saline, or orally administering, for example, a tablet, capsule or syrup containing the active ingredient.

EGCG-containing compositions of the invention can be administered simultaneously or sequentially with other nutraceuticals, foodstuffs, drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anestetics, steroids and corticosteroids.

Preferred unit dosage formulations are those containing a daily dose or unit, daily subdose, or an appropriate fraction thereof, of an agent. Therapeutic amounts can be empirically determined and will vary with the pathology being treated, the subject being treated, and the efficacy and toxicity of the agent. Similarly, suitable dosage formulations and methods of administering the agents can be readily determined by those of skill in the art.

MISCELLANEOUS AND DEFINITIONS

As used in this specification, the singular forms "a", "an", and "the" include plural references unless the context clearly dictates otherwise.

The term "administering" and "administration" is intended to mean a mode of delivery including, without limitation, oral, rectal, parenteral, subcutaneous, intravenous, intramuscular, intraperitoneal, intraarterial, transdermally or via a mucus membrane. One skilled in the art recognizes that suitable forms of oral formulation include, but are not limited to, a tablet, a pill, a capsule, a lozenge, a powder, a sustained release tablet, a liquid, a liquid suspension, a gel, a syrup, a slurry, a suspension, and the like. For example, a daily dosage can be divided into one, two or more doses in a suitable form to be administered at one, two or more times throughout a time period.

As used herein, the terms "crystallize", "recrystallize" and the like, used herein, refer to all methods suitable for forming a desired crystal form or habit or mixture or other combination thereof, and are not limited. For example, crystal slurrying, crystal precipitation, and other solvent mediated crystal transformation, with or without seeding and/or nucleation, are all encompassed by the terms "crystallize", "recrystallize" and the like as used herein.

It will be understood that a specific "effective amount" for any particular in vivo or in vitro application will depend upon a variety of factors including the activity of the specific compound employed, the age, body weight, general health, sex, and/or diet of the individual, time of administration, route of administration, rate of excretion, drug combination and the severity of the particular disease undergoing prevention or therapy.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include citric acid, lactic acid, tartaric acid, fatty acids, and the like. Salts may also be formed with bases. Such salts include salts derived from inorganic or organic bases, for example alkali metal salts such as magnesium or calcium salts, and organic amine salts such as morpholine, piperidine, dimethylamine or diethylamine salts.

As used herein, the terms "individual" and "patient" are used interchangeably to refer to any vertebrate, mammalian species, such as humans and animals. Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Human or non-human animal patients can range in age from neonates to elderly.

As used herein, the term "pharmaceutically acceptable carrier" includes any and all solvents (such as phosphate buffered saline buffers, water, saline and the like), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients can also be incorporated into the compositions. The pharmaceutical compositions of the subject invention can be formulated according to known methods for preparing pharmaceutically useful compositions. Formulations are described in a number of sources which are well known and readily available to those skilled in the art. For example, Remington's Pharmaceutical Science (Martin, E. W., 1995) describes formulations which can be used in connection with the subject invention.

As used herein, the term "reference form" is used to compare the EGCG crystal forms to a reference compound that is EGCG in a different form. The reference compound may be EGCG as a free form, or more specifically, an anhydrate or hydrate of a free form, or more specifically, for example, a hemihydrate, monohydrate, dihydrate, trihydrate, quadrahydrate, pentahydrate; or a solvate of a free form. The reference form may also be specified as crystalline or amorphous. The reference form may also be specified as the most stable EGCG polymorph known of the specified form of the reference compound.

As used herein, the term "substantially and crystallographically pure" means that other crystal forms are not analytically identifiable. In this context, analysis refers to at least one of powder X-ray diffraction, Fourier Transform infrared spectrophotometry (FT-IR), thermogravimetric analysis (TGA), differential scanning calorimetry (DSC), and single crystal X-ray diffraction, which are described below.

The term "therapeutically effective" is intended to mean an amount of a compound sufficient to substantially improve some symptom associated with a disease or a medical condition. For example, in the treatment of cancer, a compound which decreases, prevents, delays, suppresses, or arrests any symptom of the disease would be therapeutically effective. A therapeutically effective amount of a compound is not required to cure a disease but will provide a treatment for a disease such that the onset of the disease is delayed, hindered, or prevented, or the disease symptoms are ameliorated, or the term of the disease is changed or, for example, is less severe or recovery is accelerated in an individual.

The terms "treatment", "treating" and the like are intended to mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition from occurring in an individual who may be predisposed to the disease but has not yet been diagnosed as having it; (b) inhibiting the disease, (e.g., arresting its development); or (c) relieving the disease (e.g., reducing symptoms associated with the disease).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

EXAMPLES

General Analysis Procedures

X-Ray Powder Diffraction

A powder X-ray diffraction pattern for the samples was obtained using a Bruker AXS D8 diffractometer. For the PXRD analysis, the acquisition parameters were as follows: source was Cu with a K line at 1.5406 .ANG.; x-y stage was manual; collimator size was 0.3 or 0.8 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 or 0.8 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2-40 or 60 degrees; the integration chi range was 0-360 degrees; the number of chi segments was 1; the step size used was 0.02; the integration utility was cylint; normalization was used; dark counts were 8; omega offset was 180; and chi and phi offsets were 0.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably +/−0.05. The entire pattern or most of the pattern peaks may also shift by about +/−0.1 degree due to differences in calibration, settings, and other variations from instrument to instrument and from operator to operator.

For PXRD data herein, each composition of the present invention may be characterized by any one, any two, any three, any four, any five, any six, any seven, or any eight or more of the 2θ angle peaks.

DSC Analysis

DSC analysis of the samples was performed using a 2920 Differential Scanning Calorimeter (TA Instruments, New Castle, Del., U.S.A.), which uses Advantage for QW-Series, version 1.0.0.78, Thermal Advantage Release 2.0 (⁸2001 TA Instruments-Water LLC). In addition, the analysis software used was Universal Analysis 2000 for Windows 95/95/2000/NT, version 3.1 E; Build 3.1.0.40 (⁸2001 TA Instruments-Water LLC).

For the DSC analysis, the purge gas used was dry nitrogen, the reference material was an empty aluminum pan that was crimped, and the sample purge was 50 mL/minute.

DSC analysis of the sample was performed by placing ≦5 mg of sample in an aluminum pan with a crimped pan closure. The starting temperature was typically 20° C. with a heating rate of 10° C./minute, and the ending temperature was 300° C. Unless otherwise indicated, all reported transitions are as stated +/−10 degrees C.

For DSC data herein, each composition of the present invention may be characterized by any one, any two, or any three DSC transitions. The different combinations of the PXRD peaks and the DSC transitions can also be used to characterize the compositions.

TGA Analysis

TGA analysis of samples was performed using a High Resolution Thermogravimetric Analyzer 2950 (TA Instruments, New Castle, Del., U.S.A.), which uses Advantage for QW-Series, version 1.0.0.78, Thermal Advantage Release 2.0 (82001 TA Instruments-Water LLC). In addition, the analysis software used was Universal Analysis 2000 for Windows 95/95/2000/NT, version 3.1E; Build 3.1.0.40 (⁸2001 TA Instruments-Water LLC).

For all of the TGA experiments, the purge gas used was dry nitrogen, the balance purge was 40 mL/minute $N_2$, and the sample purge was 60 mL/minute $N_2$.

TGA of the sample was performed by placing 9 mg to 20 mg of sample in a platinum pan. The starting temperature was typically 20° C. with a heating rate of 10° C./minute, and the ending temperature was 400° C.

Single Crystal X-Ray Diffraction

Single crystal x-ray data were collected on a Bruker AXS SMART-APEX CCD diffractometer (M. J. Zawarotko, Department of Chemistry, University of South Florida). Lattice parameters were determined from least squares analysis. Reflection data was integrated using the program SAINT. The structure was solved by direct methods and refined by full matrix least squares using the program SHELXTL (Sheldrick, G. M. SHELXTL, Release 5.03; Siemens Analytical X-ray Instruments Inc.: Madison, Wis.).

Example 1

EGCG Crystal Form II

Epigallocatechin-3-gallate (90% pure, 65 mg, 0.141 mmol) was dissolved in 1 mL of acetonitrile solvent (99% pure, Aldrich). The resulting solution was layered on 2.5 mL of dichloromethane solvent (distilled, stored over molecular sieves). The entire solution was cooled to between −20° C. to −5° C. and allowed to stand for 72 hours. The reaction is illustrated by the following reaction scheme:

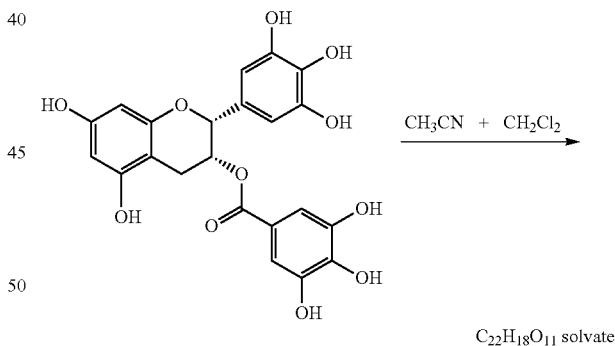

Figure 2:
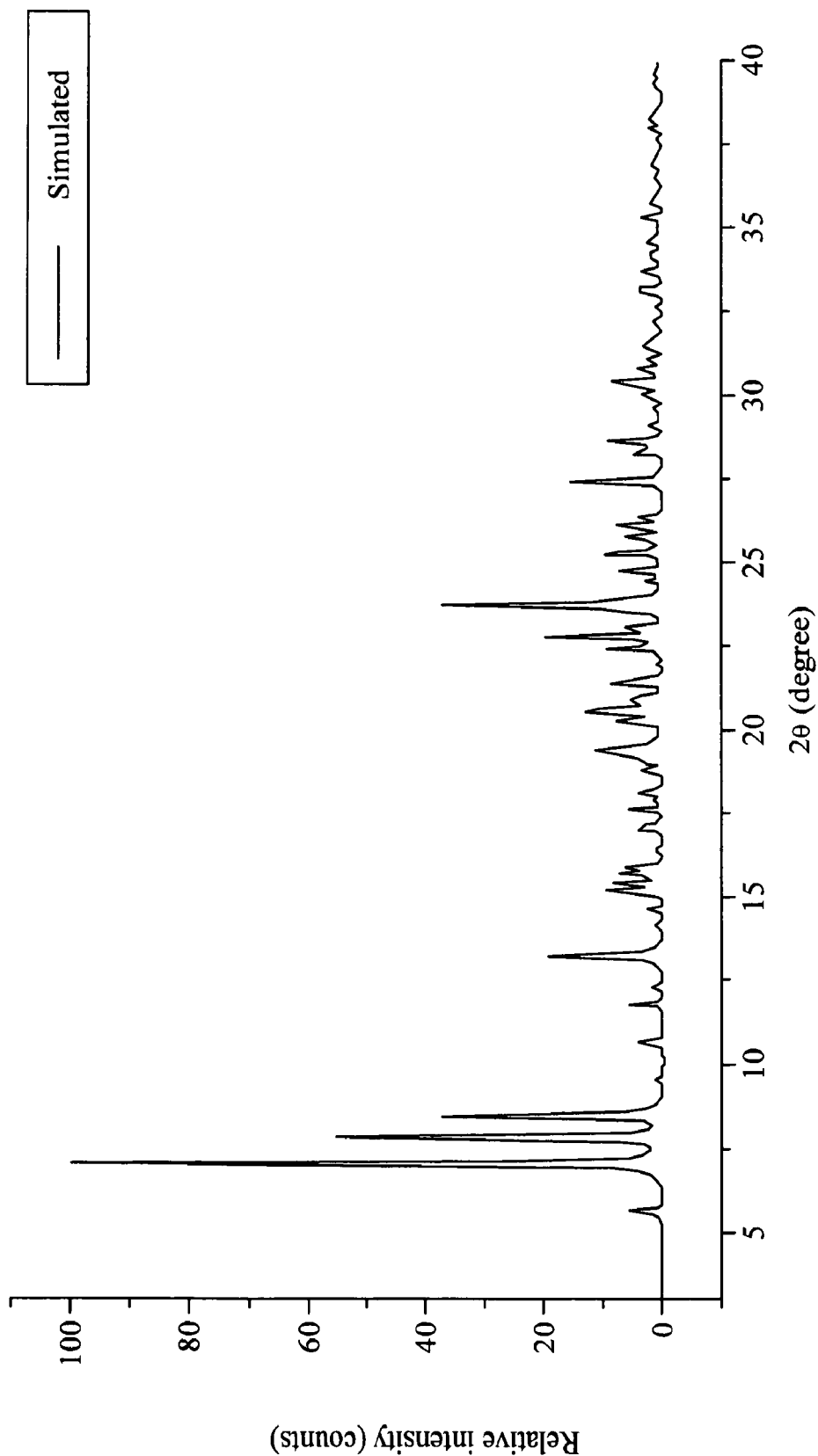
FIG. 2 shows a calculated XRPD pattern for a sample of EGCG in crystal form II as described more fully in Example 1.
Figure 3:
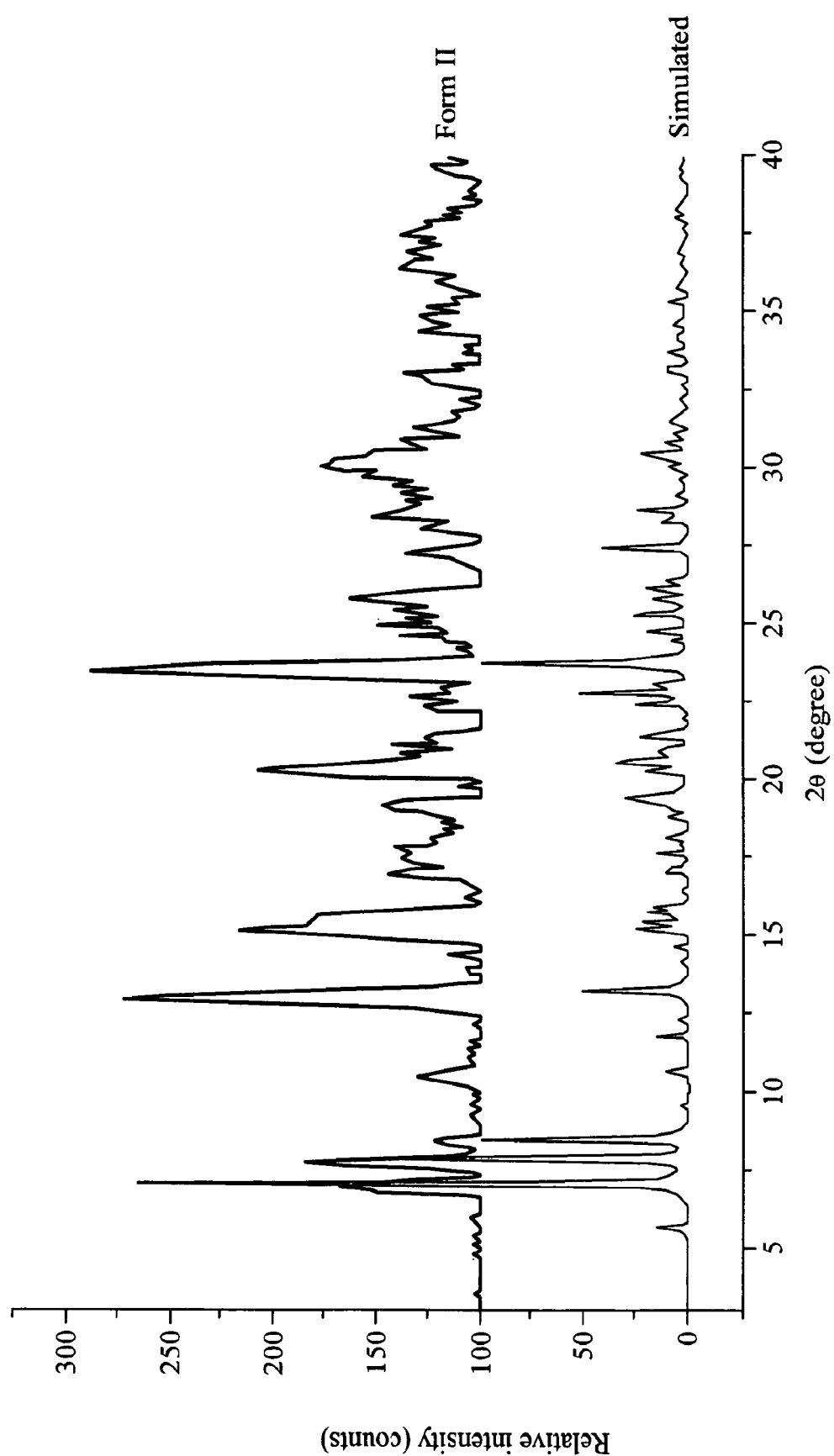
FIG. 3 shows a comparison of the experimental and calculated XRPD patterns for crystal form II as described more fully in Example 1.

The resultant colorless platelet crystals were collected and characterized using XRPD, and exhibited major peaks at about the following positions: 7.1, 7.8, 10.5, 13.0, 15.2, 20.3, 23.5, and 25.9, as shown in FIG. 1 of the accompanying drawings. FIG. 2 of the accompanying drawings shows the calculated XRPD values for Form II. FIG. 3 of the accompanying drawings is a comparison of the experimental and calculated XRPD values for EGCG Form II.

Figure 4:
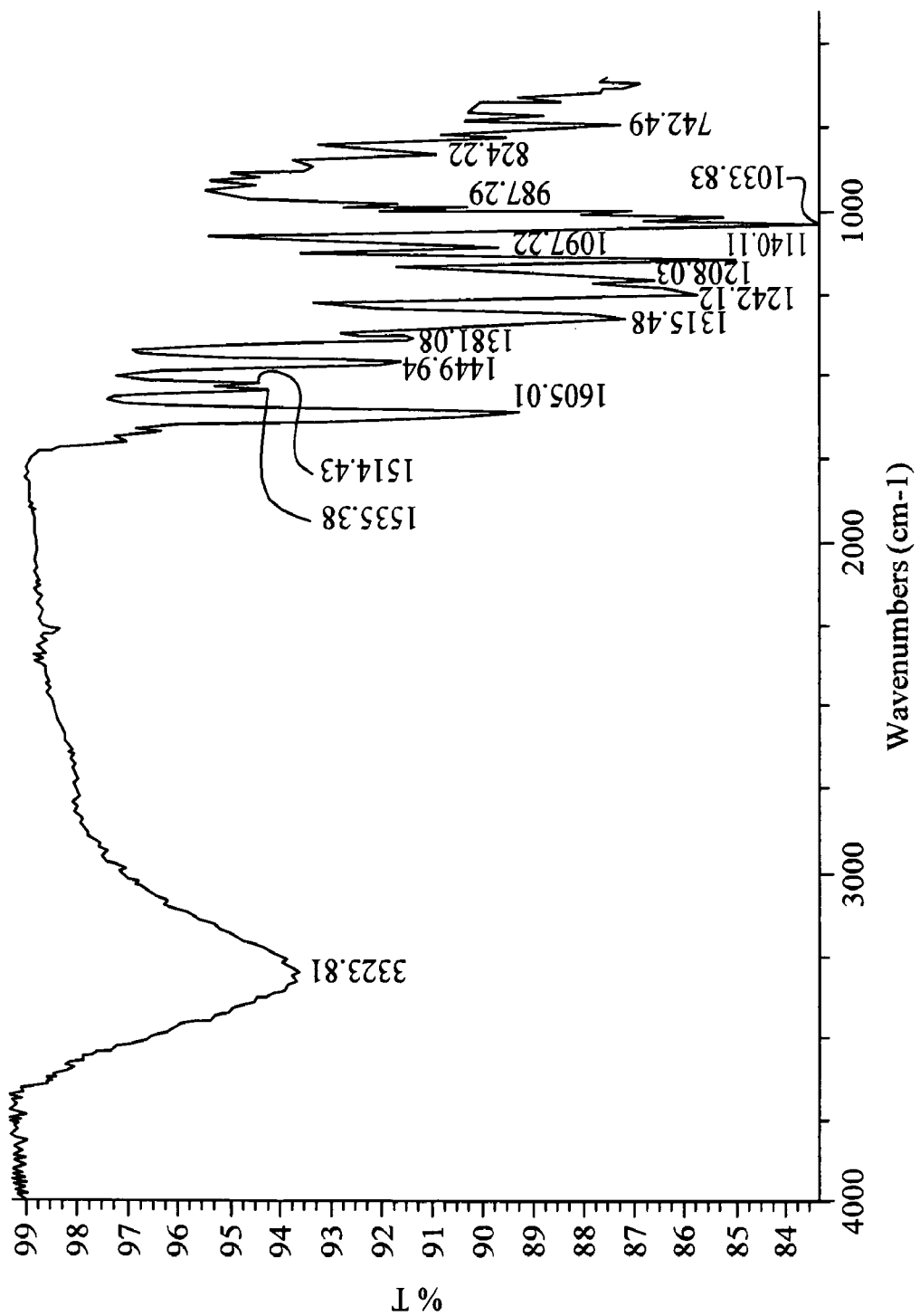
FIG. 4 shows a FT-IR spectra of a sample of EGCG in crystal form II as described more fully in Example 1.

EGCG Form II was also characterized using FT-IR. The FT-IR spectra are shown in FIG. 4 of the accompanying drawings. The major peaks in the FT-IR absorption pattern are found at about the values listed in the following table:

| Crystal Form II |
| --- |
| 742 |
| 824 |
| 987 |
| 1034 |
| 1097 |
| 1140 |
| 1208 |
| 1242 |
| 1315 |
| 1381 |
| 1450 |
| 1514 |
| 1535 |
| 1605 |
| 3324 |

Figure 5:
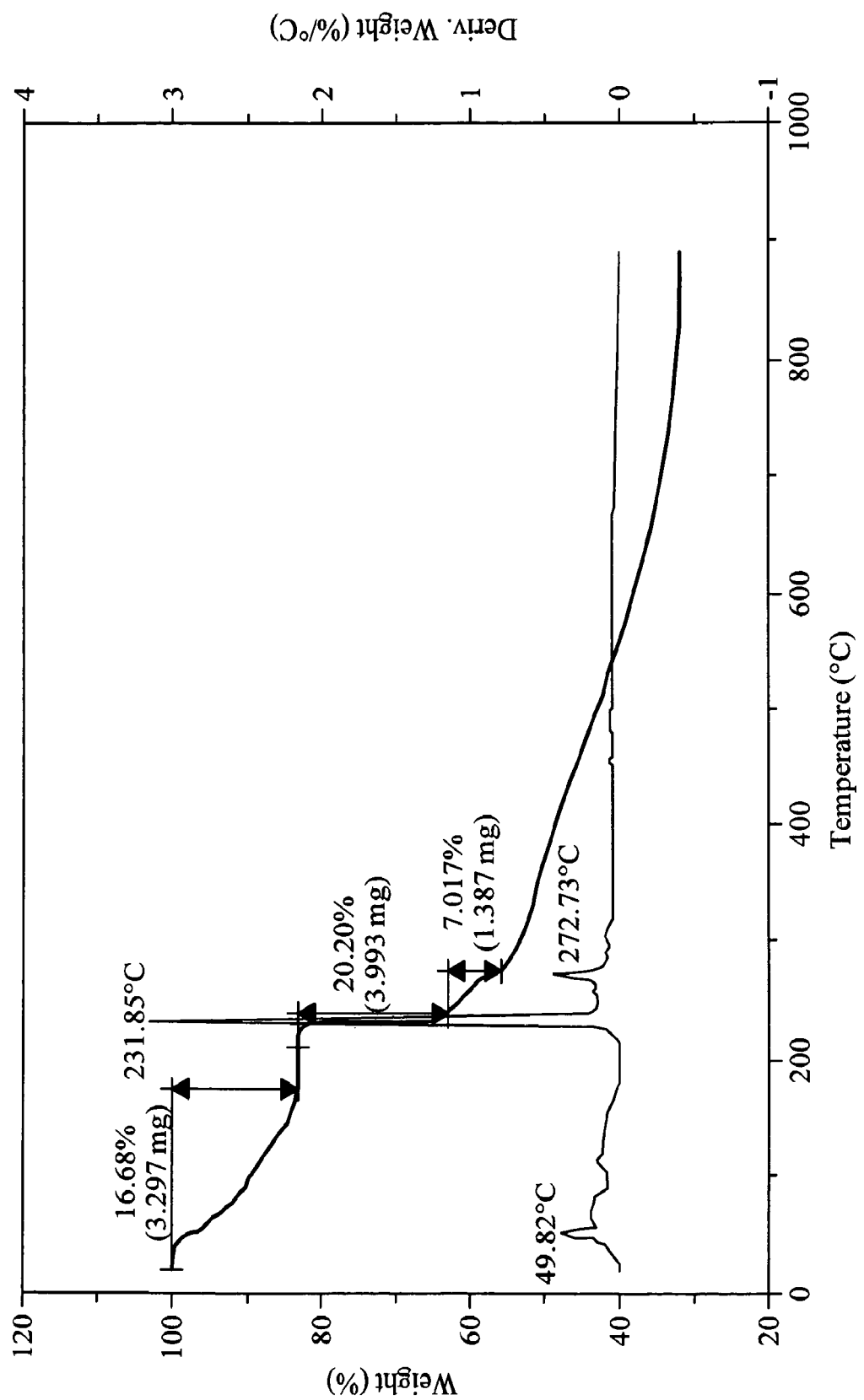
FIG. 5 shows a TGA graph of a sample of EGCG in crystal form II as described more fully in Example 1.

Crystal Form II was also characterized by TGA and DSC. The TGA graph is shown in FIG. 5 of the accompanying drawings. The DSC thermogram is shown in FIG. 6 of the accompanying drawings, with phase changes observed at about 106° C. and about 253° C.

Single crystal x-ray diffraction analysis was also performed on EGCG Form II to determine the crystal structure and physical properties thereof of Form II. The crystallographic data are shown in the following table:

| EGCG Crystal Form II•Solvate Crystallographic Data | |
| --- | --- |
| Molecular formula | $C_{24}H_{21}NO_{11}$ |
| Formula weight | 499.42 |
| Crystal system | Monoclinic |
| Space group | C2 |
| Unit cell dimensions | a = 22.876(3) Å |
| | b = 14.9054(17) Å |
| | c = 15.8886(18) Å |
| | α = 90° |
| | β = 102.688(2)° |
| | γ = 90° |
| Volume | 5285.4(10) Å$^3$ |
| Z | 8 |
| Temperature | 100(2) K |
| Density (calculated) | 1.433 Mg/m$^3$ |
| λ(Mo—Kα) | 0.71073 Å |

Figure 7:
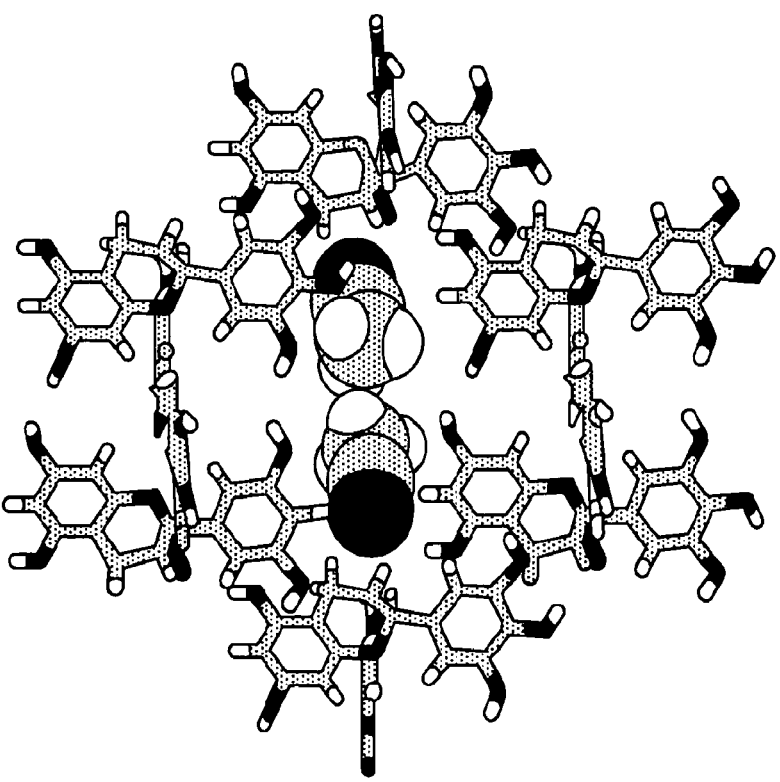
FIG. 7 shows the crystal packing structure with acetonitrile and EGCG molecules and the solvent entrapment in crystal form II as described more fully in Example 1.
Figure 7:
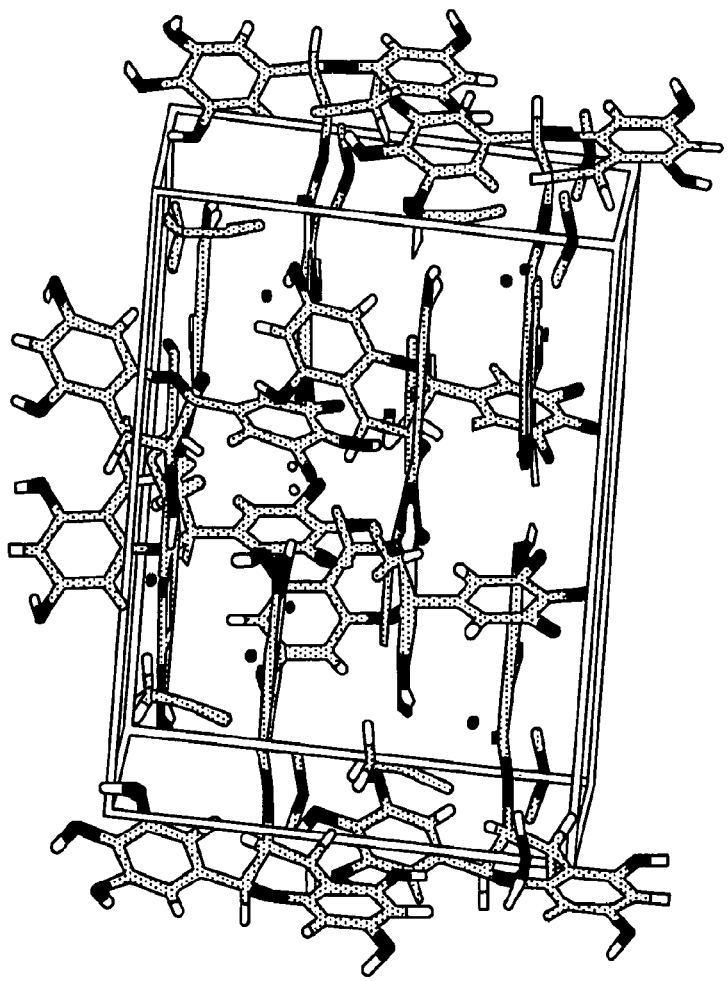
Figure 8:
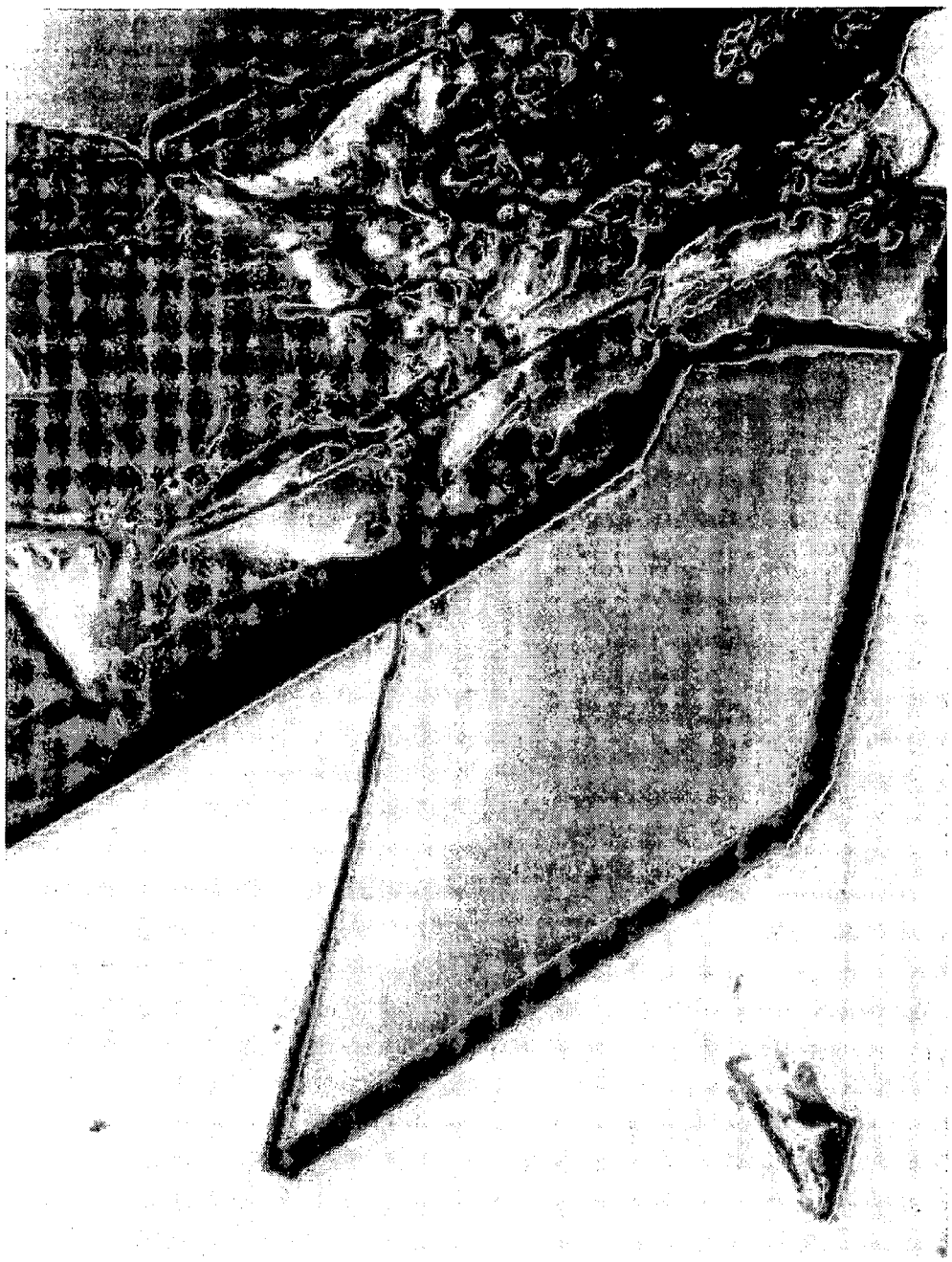
FIG. 8 is a digital microscopic image of EGCG crystal form II as described more fully in Example 1.

The three-dimensional crystal packing structure of Crystal Form II was determined to be substantially similar to that shown in FIG. 7 of the accompanying drawings. FIG. 8 of the accompanying drawings is a digital microscopic photo of Crystal Form II.

Example 2

Production of Crystal Form III of EGCG

Epigallocatechin-3-gallate (90% pure, 200 mg, 0.436 mmol) was dissolved in 2.5 mL of acetonitrile solvent (99% pure, Aldrich). The resulting solution was layered onto 6 mL of distilled dichloromethane and 2 mL of nitrobenzene. The entire solution was cooled to between −20° C. and −5° C. and allowed to stand for 48 hours. The reaction is illustrated by the following reaction scheme:

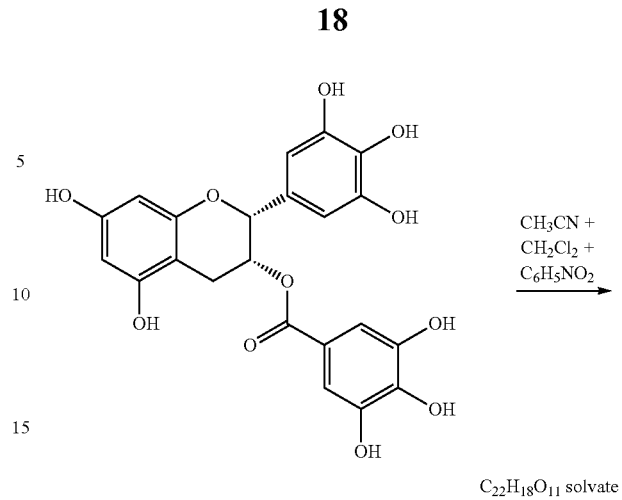

Figure 9:
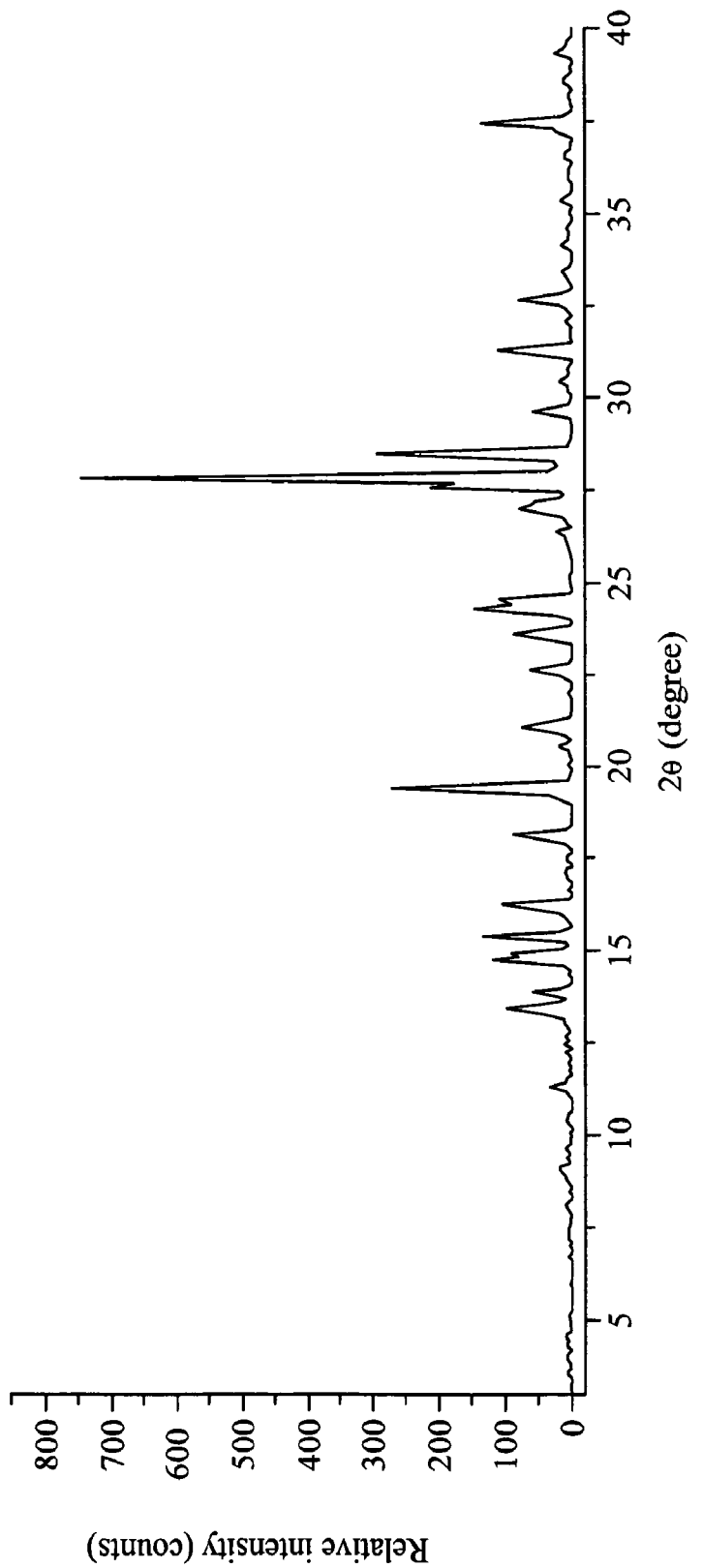
FIG. 9 shows an experimental XRPD pattern of a sample of EGCG in crystal form III, exhibiting major peaks at about the following positions: 13.4, 15.4, 19.4, 24.3, 27.8, 28.5, 31.3, and 37.5 as described more fully in Example 2.
Figure 10:
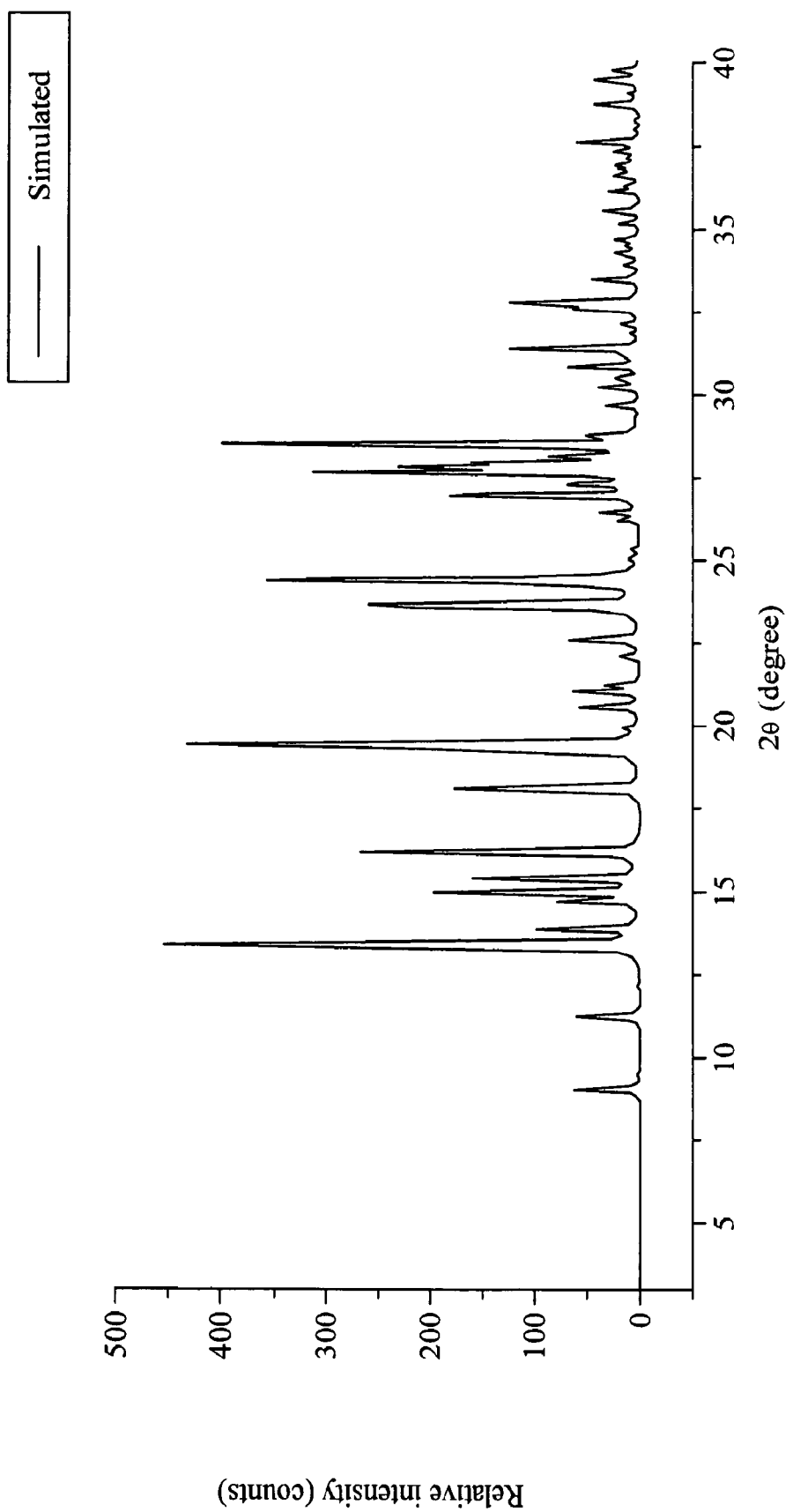
FIG. 10 shows a calculated XRPD pattern for a sample of EGCG in crystal form III as described more fully in Example 2.

The resultant yellow needle crystals were collected and characterized using XRPD, and exhibited major peaks at about the following positions: 13.4, 15.4, 19.4, 24.3, 27.8, 28.5, 31.3, and 37.5, as shown in FIG. 9 of the accompanying drawings. FIG. 10 of the accompanying drawings shows the calculated XRPD values for Form III. FIG. 11 of the accompanying drawings is a comparison of the experimental and calculated XRPD values for EGCG Form III.

Figure 12:
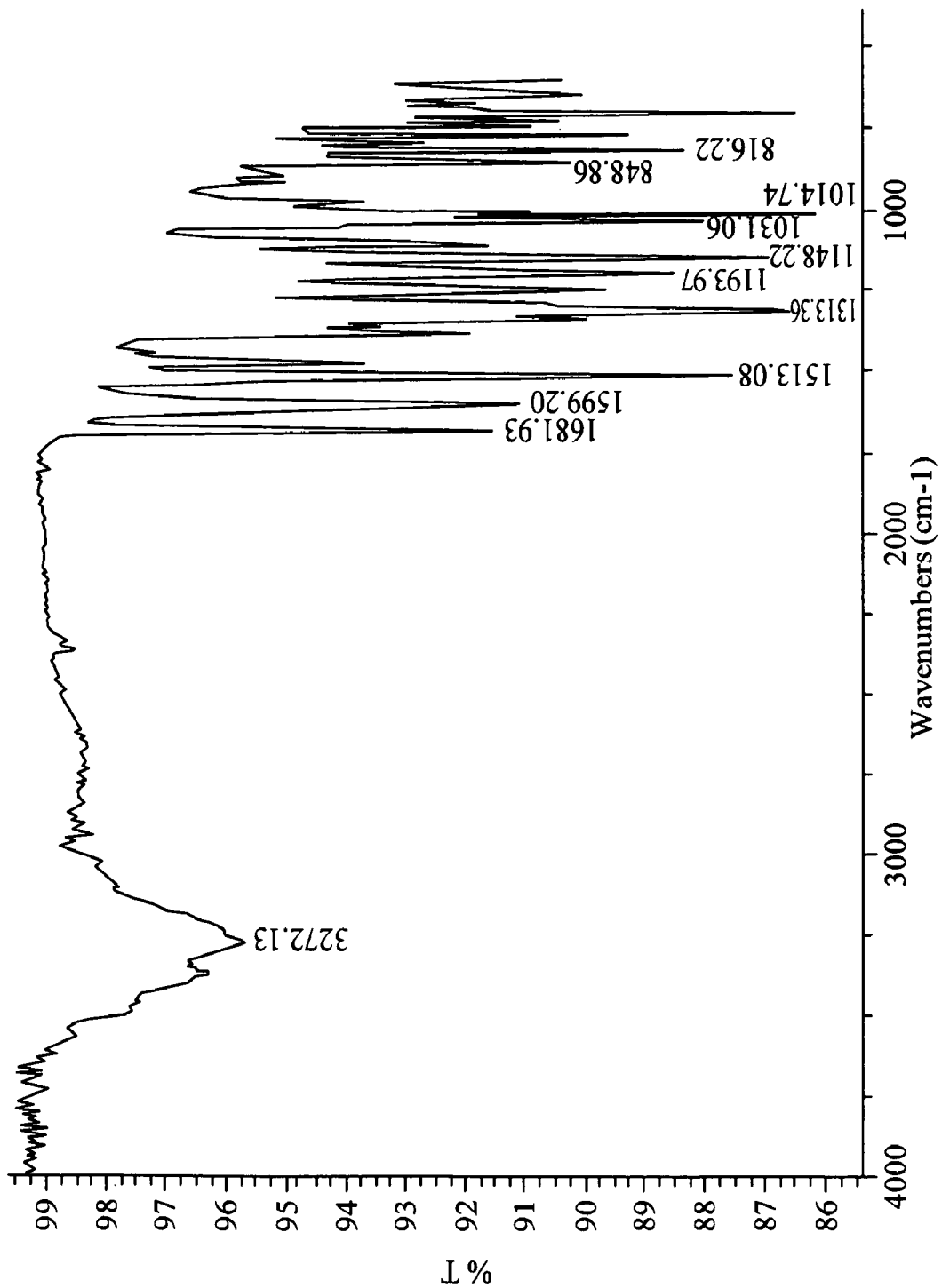
FIG. 12 shows a FT-IR spectra of a sample of EGCG in crystal form III as described more fully in Example 2.

Crystal form III of EGCG can also be discriminated by FT-IR spectra. The FT-IR spectra are shown in FIG. 12 of the accompanying drawings. The major peaks in the FT-IR absorption pattern are found at about the values listed in the following table:

| Crystal Form III |
| --- |
| 816 |
| 849 |
| 1031 |
| 1015 |
| 1148 |
| 1194 |
| 1313 |
| 1513 |
| 1599 |
| 1681 |
| 3272 |

Figure 13:
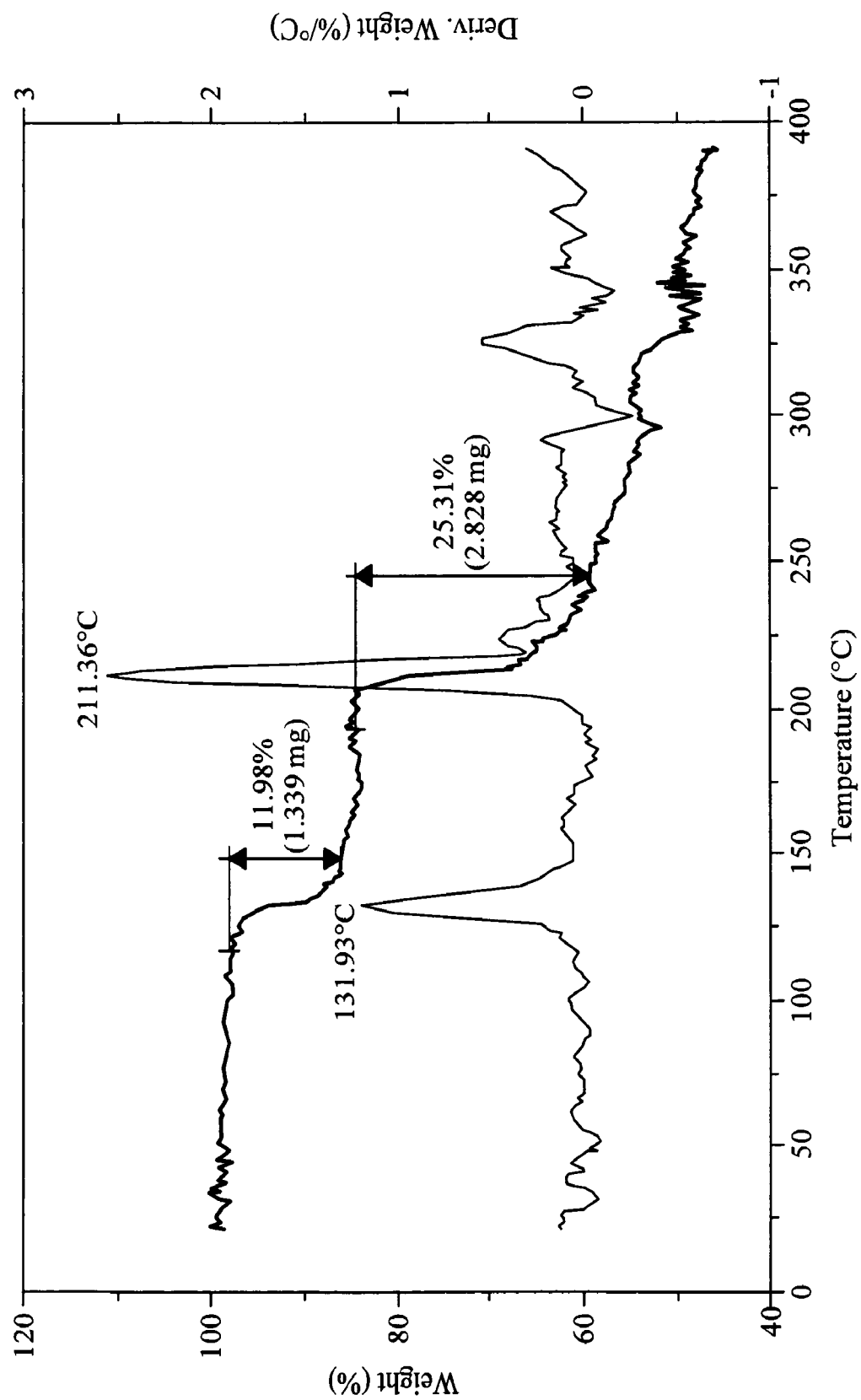
FIG. 13 shows a TGA graph of a sample of EGCG in crystal form III as described more fully in Example 2.
Figure 14:
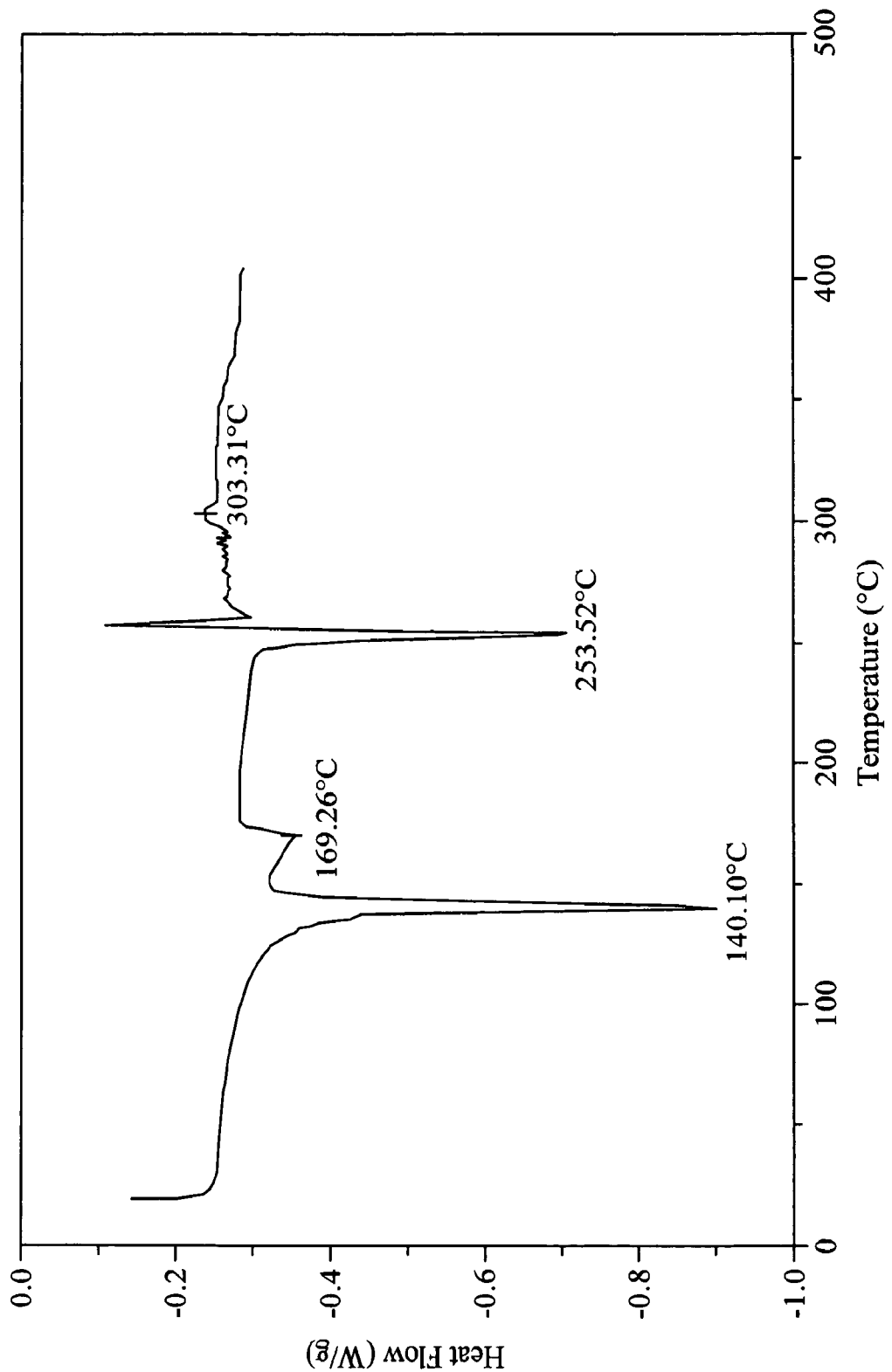
FIG. 14 shows a DSC thermogram of a sample of EGCG in crystal form III, with phase changes observed at about 140° C., about 169° C., and about 254° C. as described more fully in Example 2.

Crystal Form III was also characterized by TGA and DSC. The TGA graph is shown in FIG. 13 of the accompanying drawings. The DSC thermogram is shown in FIG. 14 of the accompanying drawings, with phase changes observed at about 140° C., about 169° C., and about 254° C.

Single crystal x-ray diffraction analysis was also performed on EGCG Form III to determine the crystal structure and physical properties thereof of Form III. The crystallographic data are shown in the following table:

| EGCG Crystal Form III•Solvate Crystallographic Data | |
| --- | --- |
| Molecular formula | $C_{28}H_{25}NO_{14}$ |
| Formula weight | 599.49 |
| Crystal system | Orthorhombic |
| Space group | P2(1)2(1)2(1) |

-continued

| EGCG Crystal Form III•Solvate Crystallographic Data | |
|---|---|
| Unit cell dimensions | a = 13.2070(14) Å |
| | b = 13.2134(14) Å |
| | c = 14.5781(16) Å |
| | α = 90° |
| | β = 90° |
| | γ = 90°; |
| Volume | 2544.0(5) Å$^3$ |
| Z | 4 |
| Temperature | 100(2) K |
| Density (calculated) | 1.565 Mg/m$^3$ |
| λ(Mo—Kα) | 0.71073 Å |

Figure 15:
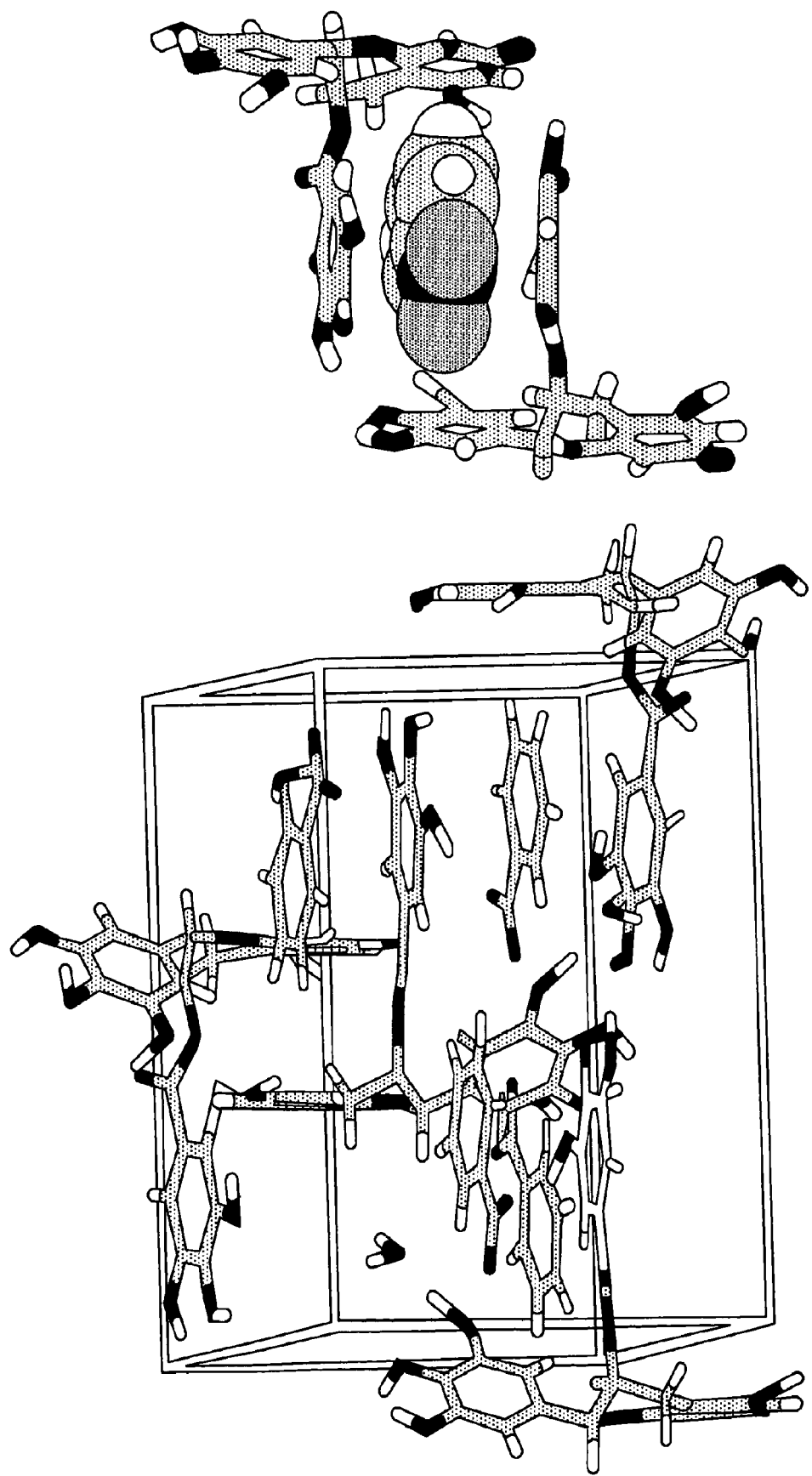
FIG. 15 shows the crystal packing structure with nitrobenzene and EGCG molecules and the solvent entrapment in crystal form III as described more fully in Example 2.
Figure 16:
FIG. 16 is a digital microscopic image of EGCG crystal form III as described more fully in Example 2.

The three-dimensional crystal packing structure of Crystal Form III was determined to be substantially similar to that shown in FIG. 15 of the accompanying drawings. FIG. 16 of the accompanying drawings is a digital microscopic photo of Crystal Form III.

Example 3

Production of Crystal Form IV of EGCG

EGCG crystal form III was heated at 120° C. for 25 minutes, resulting in a powder. This powder (45 mg, 0.098 mmol) was dissolved in 1 mL of acetonitrile solvent (99% pure, Aldrich). The solution was layered on 2.5 mL dichloromethane (distilled, stored over molecular sieves). The entire solution was cooled to 30° C.-48° C. and allowed to stand for seven days. The reaction is illustrated by the following reaction scheme:

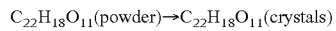

$C_{22}H_{18}O_{11}$(powder)→$C_{22}H_{18}O_{11}$(crystals)

Figure 17:
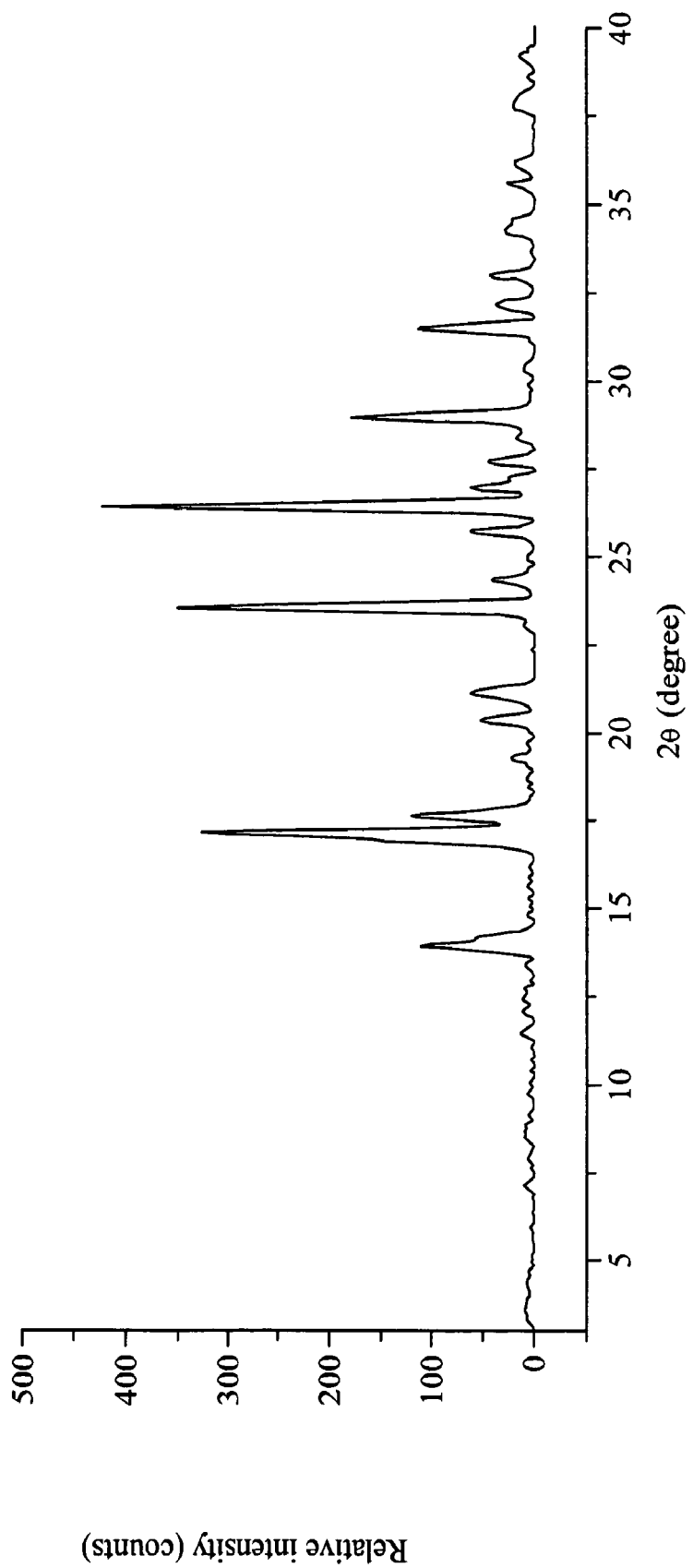
FIG. 17 shows an experimental XRPD pattern of a sample of EGCG in crystal form IV, exhibiting major peaks at about the following positions: 13.9, 17.2, 21.2, 23.6, 26.5, 29.0, and 31.5 as described more fully in Example 3.
Figure 18:
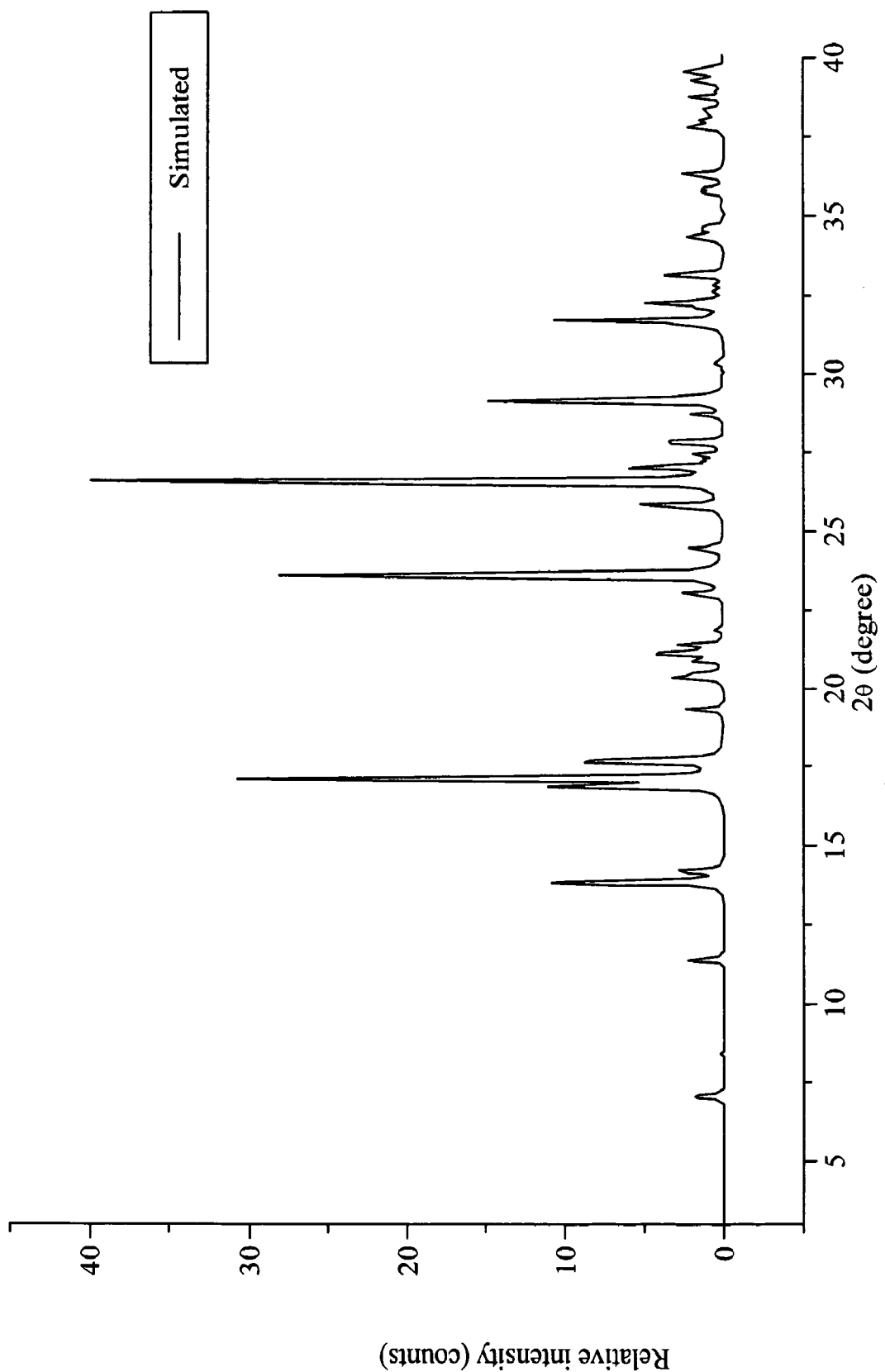
FIG. 18 shows a calculated XRPD pattern for a sample of EGCG in crystal form IV as described more fully in Example 3.
Figure 19:
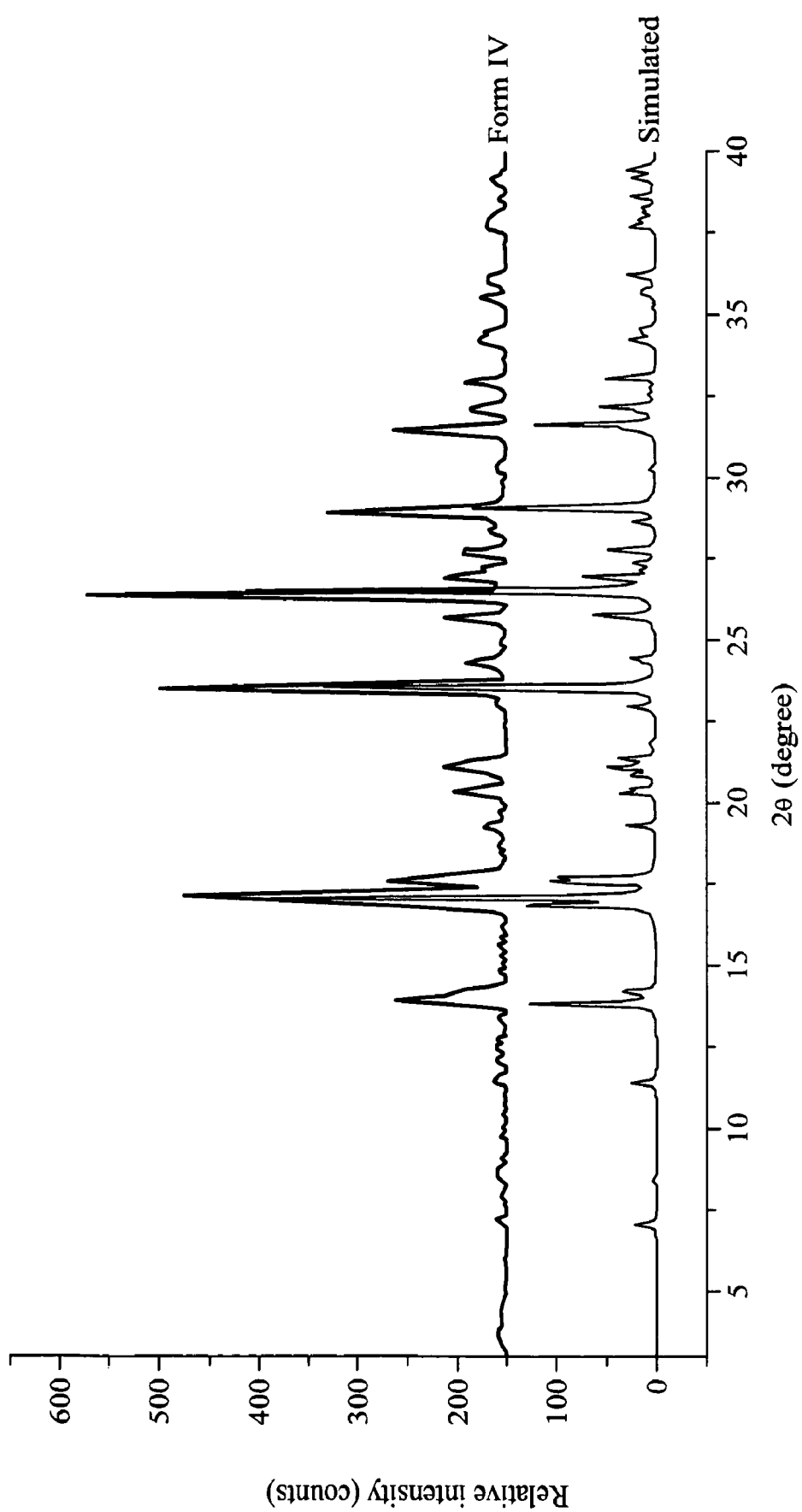
FIG. 19 shows a comparison of the experimental and calculated XRPD patterns for crystal form IV as described more fully in Example 3.

The resultant colorless needle crystals were collected and characterized using XRPD, and exhibited major peaks at about the following positions: 13.9, 17.2, 21.2, 23.6, 26.5, 29.0, and 31.5, as shown in FIG. 17 of the accompanying drawings. FIG. 18 of the accompanying drawings shows the calculated XRPD values for Form IV. FIG. 19 of the accompanying drawings is a comparison of the experimental and calculated XRPD values for EGCG Form IV.

Figure 20:
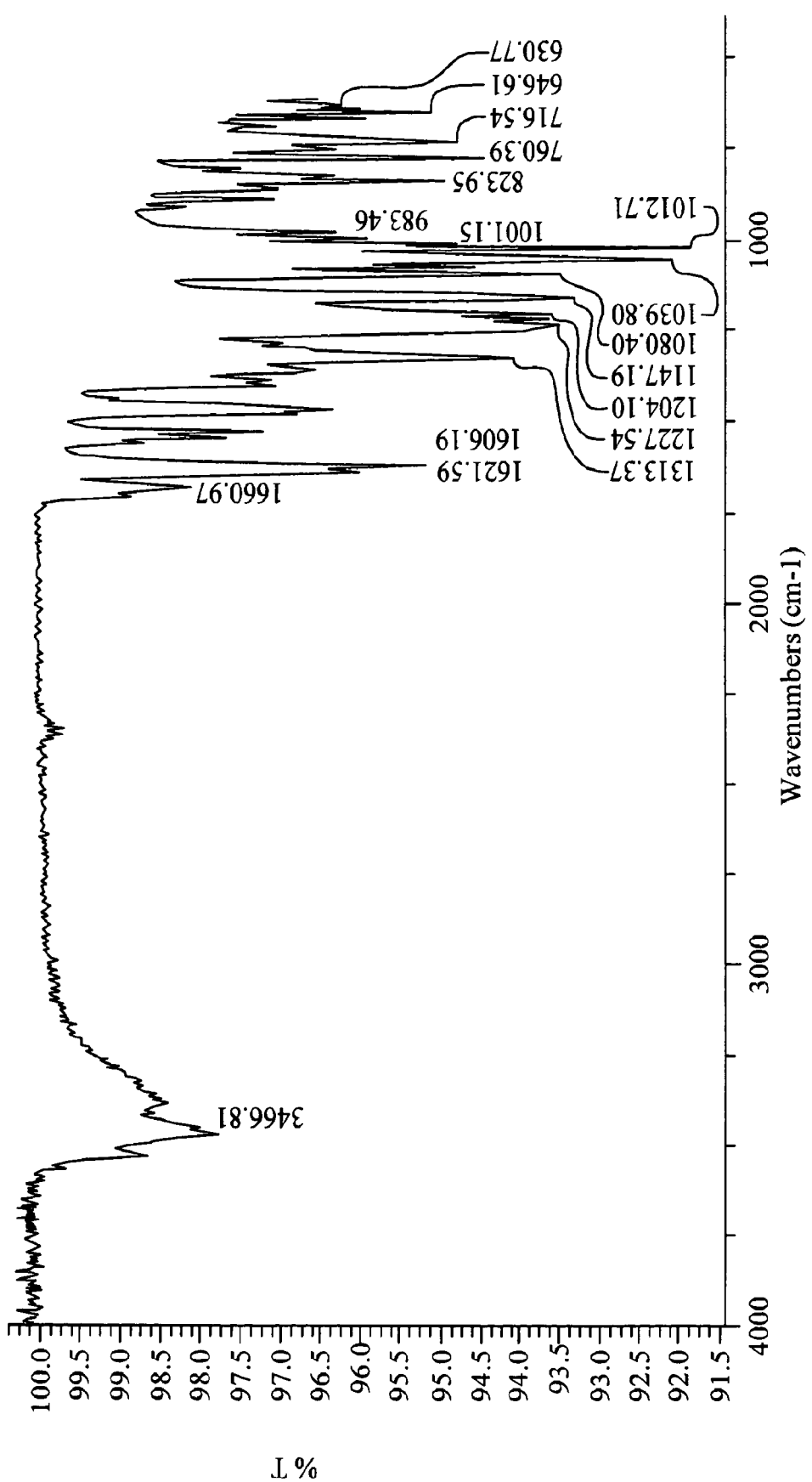
FIG. 20 shows a FT-IR spectra of a sample of EGCG in crystal form IV as described more fully in Example 3.

Crystal form IV of EGCG can also be discriminated by FT-IR spectra. The FT-IR spectra are shown in FIG. 20 of the accompanying drawings. The major peaks in the FT-IR absorption pattern are found at about the values listed in the following table:

| Crystal Form IV |
|---|
| 631 |
| 647 |
| 717 |
| 760 |
| 824 |
| 983 |
| 1001 |
| 1040 |
| 1080 |
| 1147 |
| 1204 |
| 1228 |
| 1313 |
| 1606 |
| 1622 |
| 1661 |
| 3467 |

Figure 21:
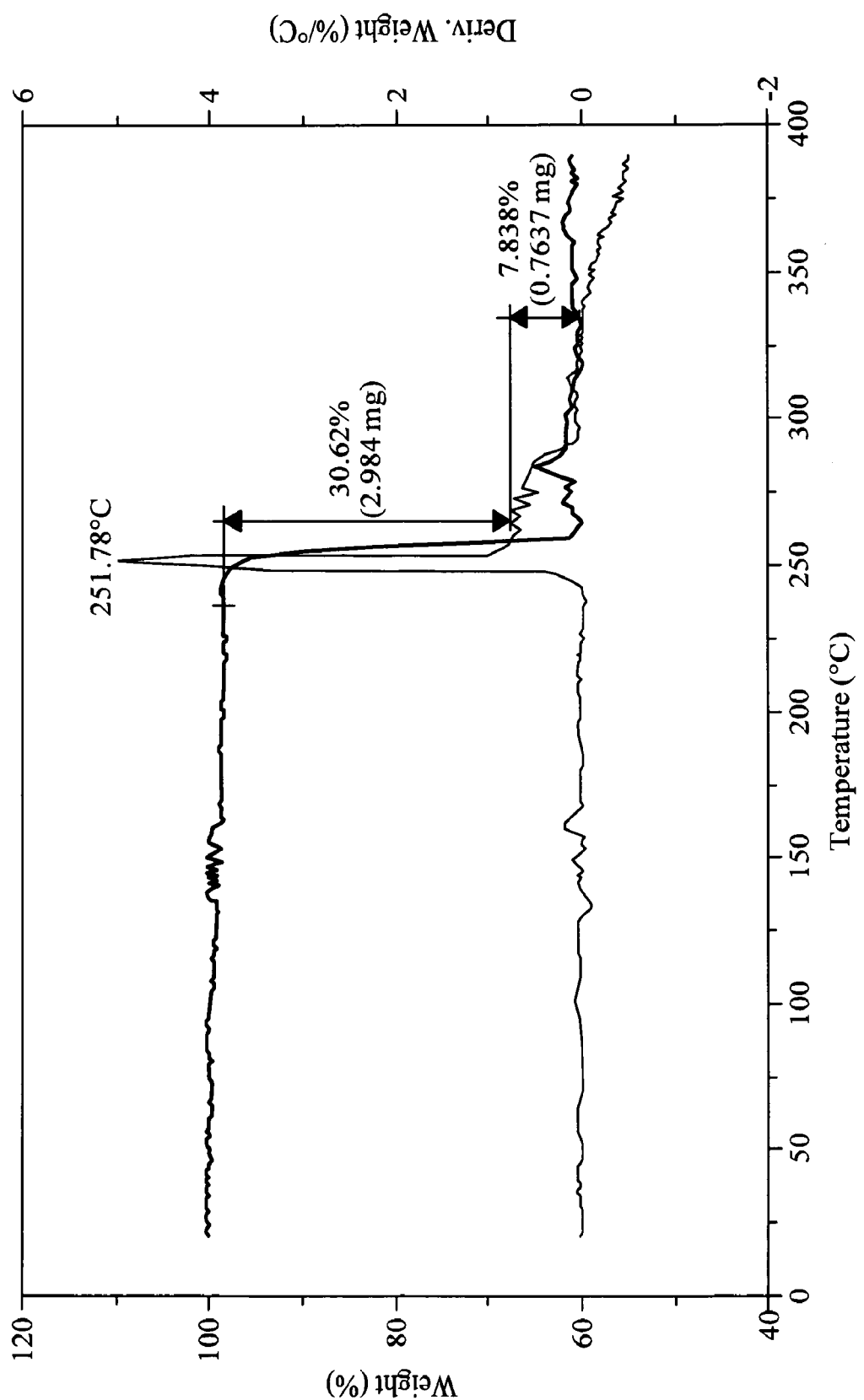
FIG. 21 shows a TGA graph of a sample of EGCG in crystal form IV as described more fully in Example 3.
Figure 22:
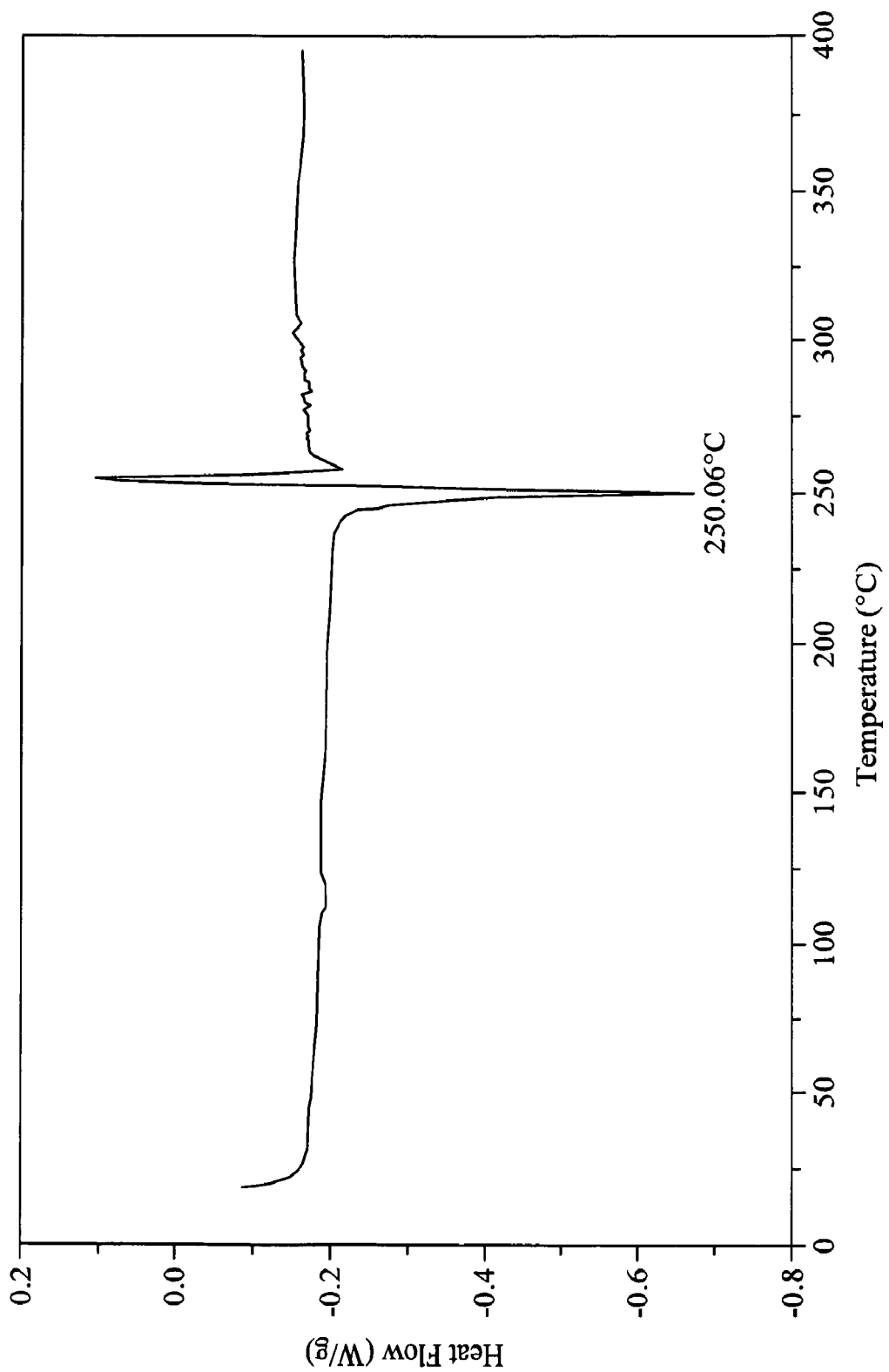
FIG. 22 shows a DSC thermogram of a sample of EGCG in crystal form IV, with a phase change observed at about 250° C. as described more fully in Example 3.

Crystal Form IV was also characterized by TGA and DSC. The TGA graph is shown in FIG. 21 of the accompanying drawings. The DSC thermogram is shown in FIG. 22 of the accompanying drawings, with a phase change observed at about 250° C.

Single crystal x-ray diffraction analysis was also performed on EGCG Form IV to determine the crystal structure and physical properties thereof of Form IV. The crystallographic data are shown in the following table:

| EGCG Crystal Form IV Crystallographic Data | |
|---|---|
| Molecular formula | $C_{22}H_{18}O_{11}$ |
| Formula weight | 458.36 |
| Crystal system | Monoclinic |
| Space group | P2(1) |
| Unit cell dimensions | a = 13.006(10) Å |
| | b = 5.686(4) Å |
| | c = 13.089(10) Å |
| | α = 90° |
| | β = 107.062(11)° |
| | γ = 90° |
| Volume | 925.4(12) Å$^3$ |
| Z | 2 |
| Temperature | 100(2) K |
| Density (calculated) | 1.645 Mg/m$^3$ |
| λ (Mo—Kα) | 0.71073 Å |

Figure 23:
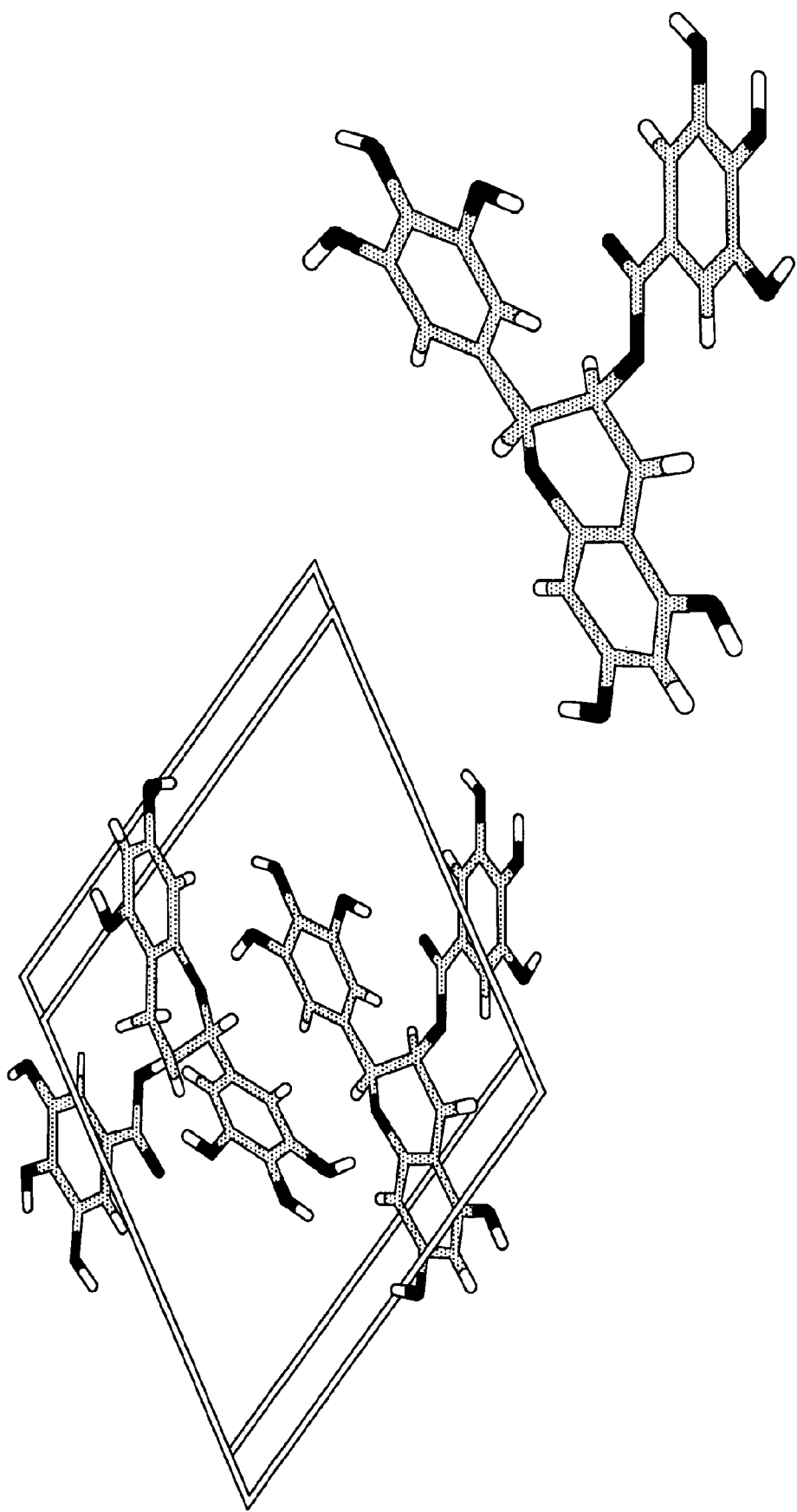
FIG. 23 shows an EGCG molecule and the crystal packing structure of EGCG in crystal form IV as described more fully in Example 3.
Figure 24:
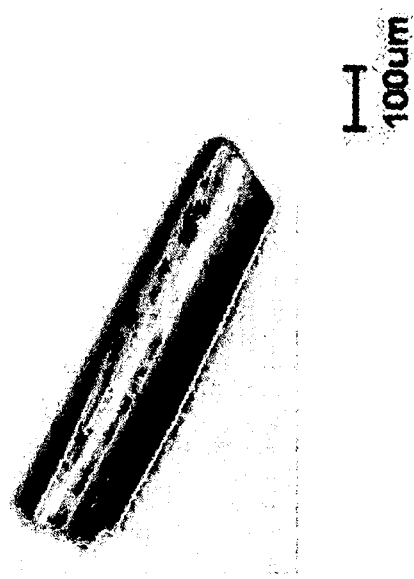
FIG. 24 is a digital microscopic image of EGCG crystal form IV as described more fully in Example 3.

The three-dimensional crystal packing structure of Crystal Form IV was determined to be substantially similar to that shown in FIG. 23 of the accompanying drawings. FIG. 24 of the accompanying drawings is a digital microscopic photo of Crystal Form IV.

What is claimed is:

1. A composition comprising crystalline epigallocatechin-3-gallate wherein the crystalline epigallocatechin-3-gallate has an XRPD pattern exhibiting major peaks at about the following positions: 13.9, 17.2, 21.2, 23.6, 26.5, 29.0, and 31.5.

2. The composition of claim 1 wherein the crystalline epigallocatechin-3-gallate contains less than 1 wt. % non-aqueous, non-solvent, non-epicatechin gallate impurities.

3. A process for the preparation of a crystal form of epigallocatechin-3-gallate, wherein said process comprises: dissolving epigallocatechin-3-gallate in a solvent to form a solution, and precipitating crystalline epigallocatechin-3-gallate from the solution wherein the crystalline epigallocatechin-3-gallate consists essentially of epigallocatechin-3-gallate having an XRPD pattern exhibiting major peaks at about the following positions: (i) 7.1, 7.8, 10.5, 13.0, 15.2, 20.3, 23.5, and 25.9, (ii) 13.4, 15.4, 19.4, 24.3, 27.8, 28.5, 31.3, and 37.5, or (iii) 13.9, 17.2, 21.2, 23.6, 26.5, 29.0, and 31.5.

4. The process of claim 3 wherein the solvent comprises acetonitrile.

5. The process of claim 3 wherein the precipitation of said crystal is initiated by adding a second solvent to the solution with or without seeding, evaporating the organic solvent from the solution, heating the solution, or cooling the solution.

6. The process of claim 5 wherein the second solvent is dichloromethane.

7. A pharmaceutical composition comprising crystalline epigallocatechin-3-gallate and a pharmaceutically acceptable excipient, wherein the crystalline epigallocatechin-3-gallate exhibits XRPD major peaks at about the following positions: (i) 13.9, 17.2, 21.2, 23.6, 26.5, 29.0, and 31.5, (ii) 7.1, 7.8, 10.5, 13.0, 15.2, 20.3, 23.5, and 25.9, or (iii) 13.4, 15.4, 19.4, 24.3, 27.8, 28.5, 31.3, and 37.5.

8. A foodstuff comprising crystalline epigallocatechin-3-gallate, wherein the crystalline epigallocatechin-3-gallate exhibits XRPD major peaks at about the following positions: (i) 13.9, 17.2, 21.2, 23.6, 26.5, 29.0, and 31.5, (ii) 7.1, 7.8, 10.5, 13.0, 15.2, 20.3, 23.5, and 25.9, or (iii) 13.4, 15.4, 19.4, 24.3, 27.8, 28.5, 31.3, and 37.5.

9. A process for treating a disease or condition resulting from oxidative stress, wherein said method comprises administering an effective amount of a composition comprising a crystal form of epigallocatechin-3-gallate to a person or animal having or predisposed to having a condition resulting from oxidative stress, wherein the crystalline epigallocatechin-3-gallate exhibits XRPD major peaks at about the following positions: (i) 13.9, 17.2, 21.2, 23.6, 26.5, 29.0, and 31.5, (ii) 7.1, 7.8, 10.5, 13.0, 15.2, 20.3, 23.5, and 25.9, or (iii) 13.4, 15.4, 19.4, 24.3, 27.8, 28.5, 31.3, and 37.5.

10. Crystalline epigallocatechin-3-gallate with less than a stoichiometric amount of water in isolated form, wherein the crystalline epigallocatechin-3-gallate exhibits XRPD major peaks at about the following positions: (i) 13.9, 17.2, 21.2, 23.6, 26.5, 29.0, and 31.5, (ii) 7.1, 7.8, 10.5, 13.0, 15.2, 20.3, 23.5, and 25.9, or (iii) 13.4, 15.4, 19.4, 24.3, 27.8, 28.5, 31.3, and 37.5.

11. The crystalline epigallocatechin-3-gallate of claim 10 wherein the crystal is solvated.

12. A process for improving animal health or nutrition, the process comprising administering to the animal a composition comprising crystalline epigallocatechin-3-gallate, wherein the crystalline epigallocatechin-3-gallate exhibits XRPD major peaks at about the following positions: (i) 13.9, 17.2, 21.2, 23.6, 26.5, 29.0, and 31.5, (ii) 7.1, 7.8, 10.5, 13.0, 15.2, 20.3, 23.5, and 25.9, or (iii) 13.4, 15.4, 19.4, 24.3, 27.8, 28.5, 31.3, and 37.5.

13. The composition of claim 1 wherein the crystalline epigallocatechin-3-gallate contains up to 20 mole % epicatechin gallate.

14. The composition of claim 10 wherein the crystalline epigallocatechin-3-gallate contains up to 20 mole % epicatechin gallate.

15. The composition of claim 11 wherein the crystalline epigallocatechin-3-gallate contains up to 20 mole % epicatechin gallate.

16. The crystalline epigallocatechin-3-gallate of claim 10 wherein the crystal is non-solvated.

17. The composition of claim 16 wherein the crystalline epigallocatechin-3-gallate contains up to 20 mole % epicatechin gallate.

* * * * *